US010124062B2

(12) United States Patent
Guthrie

(10) Patent No.: US 10,124,062 B2
(45) Date of Patent: Nov. 13, 2018

(54) METHODS OF TREATING, INHIBITING AND/OR PREVENTING AN AUDITORY IMPAIRMENT

(71) Applicant: The Department of Veterans Affairs, Washington, DC (US)

(72) Inventor: O'neil W. Guthrie, Flagstaff, AZ (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/444,147

(22) Filed: Feb. 27, 2017

(65) Prior Publication Data

US 2017/0260525 A1 Sep. 14, 2017

Related U.S. Application Data

(60) Provisional application No. 62/300,585, filed on Feb. 26, 2016.

(51) Int. Cl.
*A61K 48/00* (2006.01)
*A61K 45/06* (2006.01)
*A61K 31/713* (2006.01)
*C12N 15/11* (2006.01)

(52) U.S. Cl.
CPC ............ *A61K 45/06* (2013.01); *A61K 31/713* (2013.01); *C12N 15/11* (2013.01)

(58) Field of Classification Search
CPC .................................................... A61K 48/00
USPC ......................................................... 514/44
See application file for complete search history.

(56) References Cited

U.S. PATENT DOCUMENTS

| 5,643,890 A * | 7/1997 | Iversen | A61K 31/711 424/93.21 |
| 9,457,009 B2 | 10/2016 | Guthrie | |
| 9,889,107 B2 | 2/2018 | Guthrie | |

OTHER PUBLICATIONS

Seidman et al. (Ageing Research Review 2002: 331-343).*
Weng D, Cunin MC, Song B, Price BD, Eller MS, Gilchrest BA, Calderwood SK, Gong J. Radiosensitization of mammary carcinoma cells by telomere homolog oligonucleotide pretreatment. Breast Cancer Res. 2010;12(5):R71. doi: 10.1186/bcr2639. Epub Sep. 16, 2010. PubMed PMID: 20846433; PubMed Central PMCID: PMC3096958—*Exhibit 4 (provided concurrently by US mail)*.
Arad S, Konnikov N, Goukassian DA, Gilchrest BA. T-oligos augment UV-induced protective responses in human skin. FASEB J. Sep. 2006;20(11):1895-7. Epub Jul. 28, 2006. PubMed PMID: 16877521—*Exhibit 5 (provided concurrently by US mail)*.
Coleman C, Levine D, Kishore R, Qin G, Thorne T, Lambers E, Sasi SP, Yaar Gilchrest BA, Goukassian DA. Inhibition of melanoma angiogenesis by telomere homolog oligonucleotides. J Oncol. 2010;2010:928628. doi:10.1155/2010/928628. Epub Jun. 28, 2010. PubMed PMID: 20652008; PubMed Central PMCID: PMC2906154—*Exhibit 6 (provided concurrently by US mail)*.
Eller MS, Liao X, Liu S, Hanna K, Backvall H, Opresko PL, Bohr VA, Gilchrest BA. A role for WRN in telomere-based DNA damage responses. Proc Natl Acad Sci USA. Oct. 10, 2006;103(41):15073-8. Epub Oct. 2, 2006. PubM ed PMID: 17015833; PubMed Central PMCID: PMC1586178—*Exhibit 7 (provided concurrently by US mail)*.
Gilchrest BA, Eller MS. The tale of the telomere: implications for prevention and treatment of skin cancers. J Investig Dermatol Symp Proc. Nov. 2005;10(2):124-30. Review. PubMed PMID: 16363064—*Exhibit 8 (provided concurrently by US mail)*.
Gnanasekar M, Thirugnanam S, Zheng G, Chen A, Ramaswamy K.T-oligo induces apoptosis in advanced prostate cancer cells. Oligonucleotides. Sep. 2009;19(3):287-92. doi: 10.1089/oli.2009.0179. PubMed PMID: 19642913—*Exhibit 9 (provided concurrently by US mail)*.
Guthrie 2017 Functional consequences of inducible genetic elements from the p53 SOS response in a mammalian organ system. Experimental Cell Research 359 (2017) 50-61—*Exhibit 10 (provided concurrently by US mail)*.
Guthrie OW, Xu H. Noise exposure potentiates the subcellular distribution of nucleotide excision repair proteins within spiral ganglion neurons. Hear Res. Dec. 2012;294(1-2):21-30. doi: 10.1016/j.heares.2012.09.001. Epub Sep. 27, 2012. PubMed PMID: 23022597—*Exhibit 11 (provided concurrently by US mail)*.
Guthrie OW, Xu H. Reduced phosphorylation of histone variant H2Ax in the organ of Corti is associated with otoprotection from noise injury. Otolaryngology, 2013, 3, 131. doi: 10.4172/2161-119X.1000131—*Exhibit 12 (provided concurrently by US mail)*.
Guthrie OW. Preincision complex-I from the excision nuclease reaction among cochlear spiral limbus and outer hair cells. J Mol Histol. Dec. 2008;39(6):617-25. doi: 10.1007/s10735-008-9202-1. Epub Nov. 1, 2008. PubMed PMID: 18979173—*Exhibit 13 (provided concurrently by US mail)*.
Hadshiew I, Barre K, Bodo E, Funk W, Paus R. T-oligos as differential modulators of human scalp hair growth and pigmentation: a new "time lapse system" for studying human skin and hair follicle biology in vitro? Arch Dermatol Res.Apr. 2008;300(4):155-9. doi: 10.1007/s00403-008-0833-6. Epub Feb. 1, 2008. PubMed PMID: 18239924—*Exhibit 14 (provided concurrently by US mail)*.
Hu BH, Henderson D, Nicotera TM. Extremely rapid induction of outer hair cell apoptosis in the chinchilla cochlea following exposure to impulse noise. Hear Res. Jan. 2006;211(1-2):16-25. Epub Oct. 10, 2005. PubMed PMID: 16219436—*Exhibit 15 (provided concurrently by US mail)*.
Kamio T, Watanabe K, Okubo K. Acoustic stimulation promotes DNA fragmentation in the Guinea pig cochlea. J Nippon Med Sch. 2012;79(5):349-56. PubMed PMID:23123391—*Exhibit 16 (provided concurrently by US mail)*.

(Continued)

Primary Examiner — Kimberly Chong
(74) Attorney, Agent, or Firm — Adriano & Associates

(57) ABSTRACT

The present invention provides methods of treating an auditory impairment associated with outer hair cells of the cochlea in a subject. The method may comprise administering to said subject an effective amount of a composition comprising, as an active agent, an oligonucleotide sequence having a portion of a mammalian telomere sequence so as to reduce the auditory impairment thereby treating the auditory impairment in the subject.

7 Claims, 8 Drawing Sheets

Specification includes a Sequence Listing.

(56) References Cited

OTHER PUBLICATIONS

Le Prell CG, Yamashita D, Minami SB, Yamasoba T, Miller JM. Mechanisms of noise-induced hearing loss indicate multiple methods of prevention. Hear Res. Apr. 2007;226(1-2):22-43. Epub Dec. 4, 2006. Review. PubMed PMID: 17141991; PubMed Central PMCID: PMC1995566—*Exhibit 17 (provided concurrently by US mail)*.

Lee MS, Yaar M, Eller MS, Runger TM, Gao Y, Gilchrest BA. Telomeric DNA induces p53-dependent reactive oxygen species and protects against oxidative damage. J Dermatol Sci. Dec. 2009;56(3):154-62. doi: 10.1016/j.jdermsci.2009.08.008. Epub Nov. 10, 2009. PubMed PMID: 19906512; PubMed Central PMCID: PMC2844100—*Exhibit 18 (provided concurrently by US mail)*.

Li GZ, Eller MS, Hanna K, Gilchrest BA. Signaling pathway requirements for induction of senescence by telomere homolog oligonucleotides. Exp Cell Res. Dec. 10, 2004;301(2):189-200. PubMed PMID: 15530855 —*Exhibit 19 (provided concurrently by US mail)*.

Lindblad AC, Rosenhall U, Olofsson A, Hagerman B. Tinnitus and Other Auditory Problems—Occupational Noise Exposure below Risk Limits May Cause Inner Ear Dysfunction. PLoS One. May 14, 2014;9(5):e97377 —*Exhibit 20 (provided concurrently by US mail)*.

Longe HO, Romesser PB, Rankin AM, Faller DV, Eller MS, Gilchrest BA, Denis GV. Telomere homolog oligonucleotides induce apoptosis in malignant but not in normal lymphoid cells: mechanism and therapeutic potential. Int J Cancer. Jan. 15, 2009;124(2):473-82. doi: 10.1002/ijc .23946. PubMed PMID: 19003960; PubMed Central PMCID: PMC2888476—*Exhibit 21 (provided concurrently by US mail)*.

Marwaha V, Chen YH, Helms E, Arad S, Inoue H, Bord E, Kishore R, Sarkissian RD, Gilchrest BA, Goukassian DA. T-oligo treatment decreases constitutive and UVB-induced COX-2 levels through p53- and NFkappaB-dependent repression of the COX-2 promoter. J Biol Chem. Sep. 16, 2005;280(37):32379-88. Epub Jul. 26, 2005. PubMed PMID: 16046401—*Exhibit 22 (provided concurrently by US mail)*.

Mulnix RE, Pitman RT, Retzer A, Bertram C, Arasi K, Crees Z, Girard J, Uppada SB, Stone AL, Puri N. hnRNP C1/C2 and Pur-beta proteins mediate induction of senescence by oligonucleotides homologous to the telomere overhang. Onco Targets Ther. Dec. 18, 2013;7:23-32. doi: 10.2147/0 TT.S54575. eCollection 2013. PubMed PMID: 24379680; PubMed Central PMCID: PMC3872271—*Exhibit 23 (provided concurrently by US mail)*.

Nelson DI, Nelson RY, Concha-Barrientos M, Fingerhut M. The global burden of occupational noise-induced hearing loss. Am J Ind Med. Dec. 2005;48(6):446-58. PubMed PMID: 16299704—*Exhibit 24 (provided concurrently by US mail)*.

Ohlemiller KK. Recent findings and emerging questions in cochlear noise injury. Hear Res. Nov. 2008;245(1-2):5-17. doi: 10.1016/j.heares.2008.08.007. Epub Aug. 29, 2008. Review. PubMed PMID: 18790034; PubMed Central PMCID: PMC2610263—*Exhibit 25 (provided concurrently by US mail)*.

Oishi N, Schacht J. Emerging treatments for noise-induced hearing loss. Expert Opin Emerg Drugs. Jun. 2011;16(2):235-45. doi: 10.1517/14728214.2011.552427. Epub Jan. 20, 2011. Review. PubMed PMID: 21247358; PubMed Central PMCID: PMC3102156—*Exhibit 26 (provided concurrently by US mail)*.

Pitman RT, Wojdyla L, Puri N. Mechanism of DNA damage responses induced by exposure to an oligonucleotide homologous to the telomere overhang in melanoma. Oncotarget. May 2013;4(5):761-71. PubMed PMID: 23800953; PubMed Central PMCID: PMC3742836—*Exhibit 27 (provided concurrently by US mail)*.

Pun N, Pitman RT, Mulnix RE, Erickson T, Iness AN, Vitali C, Zhao Y, Salgia R. Non-small cell lung cancer is susceptible to induction of DNA damage responses and inhibition of angiogenesis by telomere overhang oligonucleotides. Cancer Lett. Feb. 1, 2014;343(1):14-23. doi: 10.1016/j.canlet.2013.09.010. Epub Sep. 14, 2013. PubMed PMID: 24041868—*Exhibit 28 (provided concurrently by US mail)*.

Rankin AM, Faller DV, Spanjaard RA. Telomerase inhibitors and 'T-oligo'as cancer therapeutics: contrasting molecular mechanisms of cytotoxicity. Anticanc er Drugs. Apr. 2008;19(4):329-38. doi: 10.1097/CAD.0b013e3282f5d4c2. Review. PubMed PMID: 18454043—*Exhibit 29 (provided concurrently by US mail)*.

Rankin AM, Forman L, Sarkar S, Faller DV. Enhanced cytotoxicity from deoxyguanosine-enriched T-oligo in prostate cancer cells. Nucleic Acid Ther. Oct. 2013;23(5):311-21. doi: 10.1089/nat.2013.0420. Epub Aug. 24, 2013. PubMed PMID: 23971906; PubMed Central PMCID: PMC3760086—*Exhibit 30 (provided concurrently by US mail)*.

Rankin AM, Sarkar S, Faller DV. Mechanism of T-oligo-induced cell cycle arrest in Mia-PaCa pancreatic cancer cells. J Cell Physiol. Jun. 2012;227(6):2586-94. doi: 10.1002/jcp.22997. PubMed PMID: 21898405; PubMed Central PMCID: PMC3251650—*Exhibit 31 (provided concurrently by US mail)*.

Ruden M, Puri N. Novel anticancer therapeutics targeting telomerase. Cancer Treat Rev. Aug. 2013;39(5):444-56. doi: 10.1016/j.ctrv .2012.06.007. Epub Jul. 26, 2012. Review. PubMed PMID: 22841437 —*Exhibit 32 (provided concurrently by US mail)*.

Sarkar S, Faller DV. T-oligos inhibit growth and induce apoptosis in human ovarian cancer cells. Oligonucleotides. Feb. 2011;21(1):47-53. doi: 10.1089/oli.2010.0259. Epub Jan. 31, 2011. PubMed PMID: 21281128; PubMed Central PMCID: PMC3116203—*Exhibit 33 (provided concurrently by US mail)*.

Shen H, Cao J, Hong Z, Liu K, Shi J, Ding L, Zhang H, Du C, Li Q, Zhang Z, Zhu B. A functional Ser326Cys polymorphism in hOGG1 is associated with noise-induced hearing loss in a Chinese population. PLoS One. Mar. 5, 2014;9(3):e89662. PubMed PMID: 24599382; PubMed Central PMCID: PMC3943766—*Exhibit 34 (provided concurrently by US mail)*.

Uppada SB, Erickson T, Wojdyla L, Moravec DN, Song Z, Cheng J, Puri N. Novel delivery system for T-oligo using a nanocomplex formed with an alpha helical peptide for melanoma therapy. Int J Nanomedicine. 2014;9:43-53. doi: 10.2147/IJNN.S55133.Epub Dec. 17, 2013. PubMed PMID: 24391441; PubMed Central PMCID: PMC3879016—*Exhibit 35 (provided concurrently by US mail)*; and.

Van Campen LE, Murphy WJ, Franks JR, Mathias PI, Toraason MA. Oxidative DNA damage is associated with intense noise exposure in the rat. Hear Res. Feb. 2002;164(1-2):29-38. PubMed PMID: 11950522—*Exhibit 36 (provided concurrently by US mail)*.

\* cited by examiner

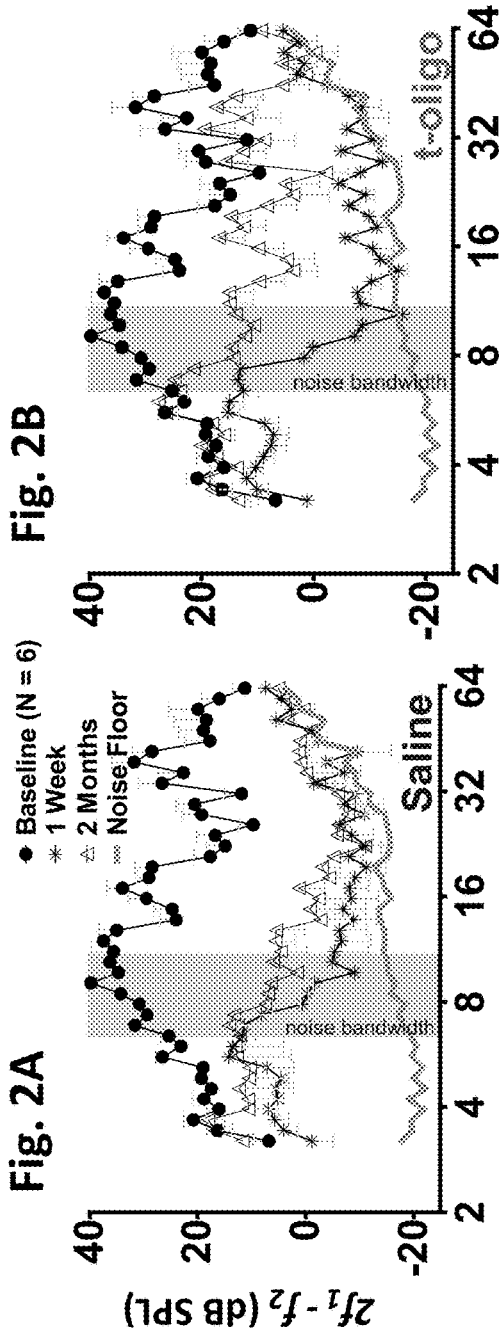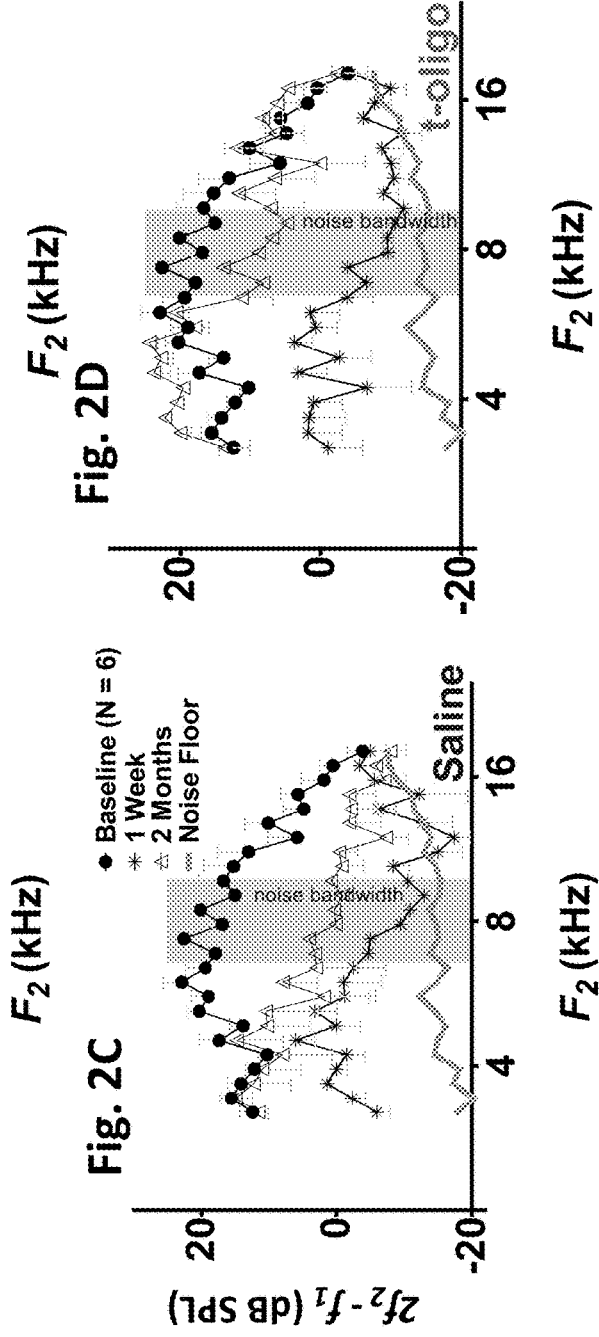

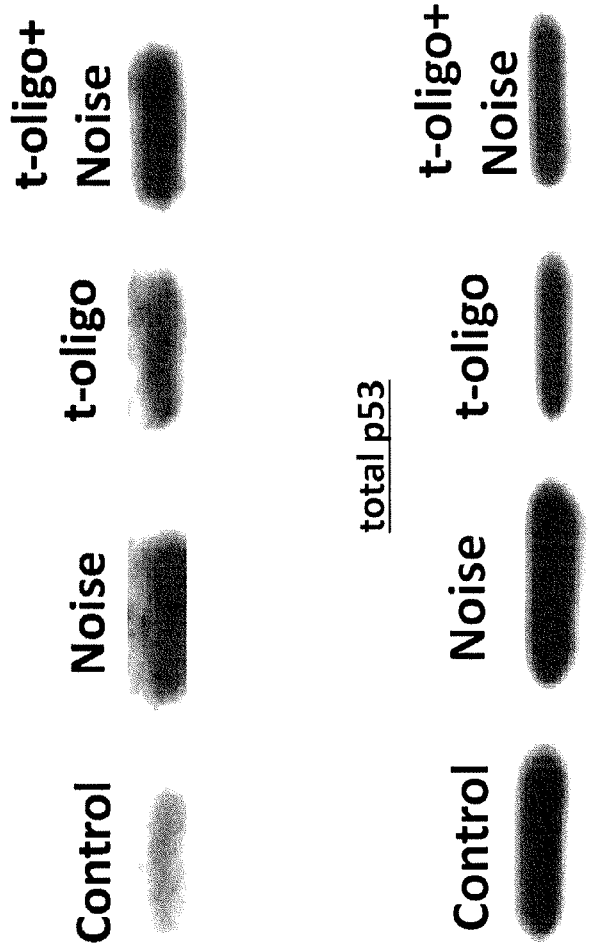

Fig. 4: phosphorylated (activated) p53 total p53

Western blot data: under normal conditions p53 is expressed in the cochlea with low activation. After noise exposure there is significant activation with some increase in total p53. T-oligo treatment increases the activation of p53 but lowers the total amount of p53 (probably to prevent apoptosis). T-oligo+noise illicits the same results.

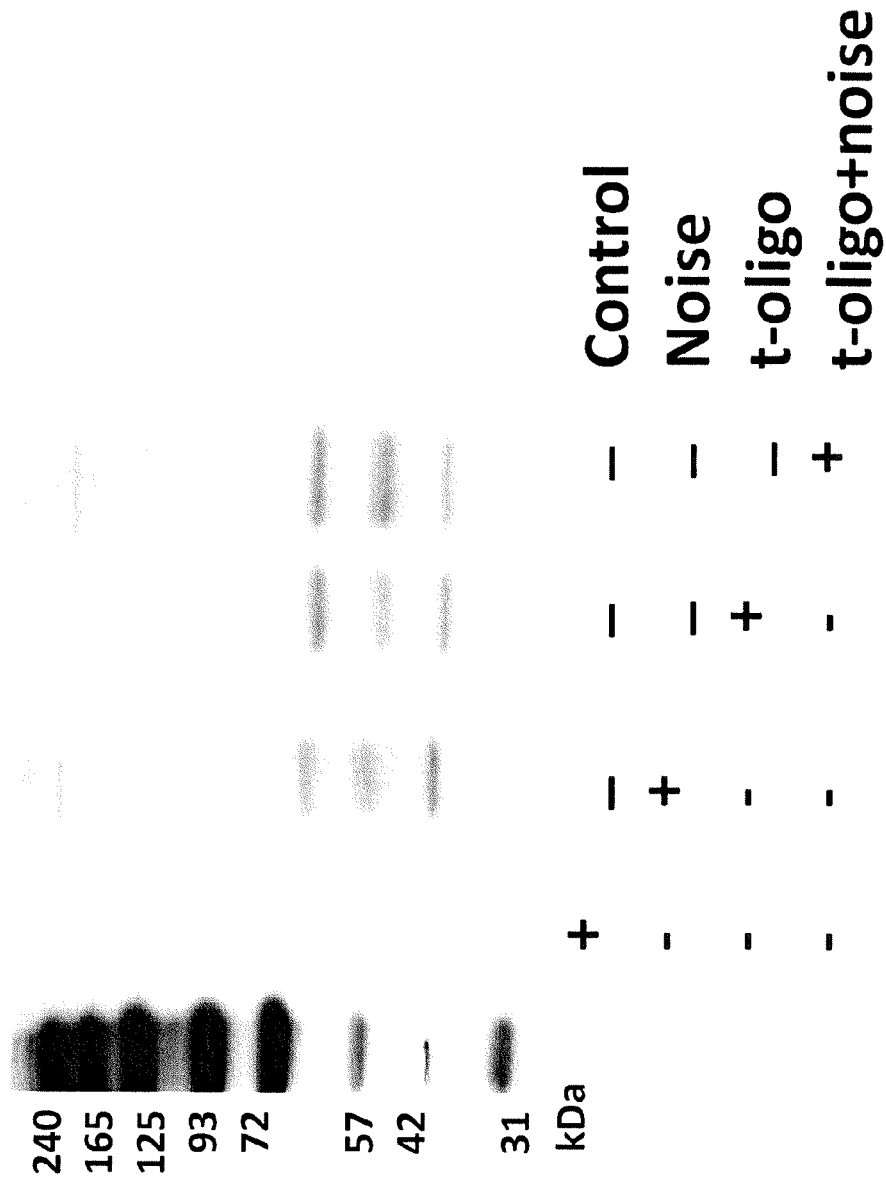
Fig. 5: ATM/ATR/DNA-Pk phosphorylation of consensus target motifs; Leu(Ser*/Thr*)Gln.

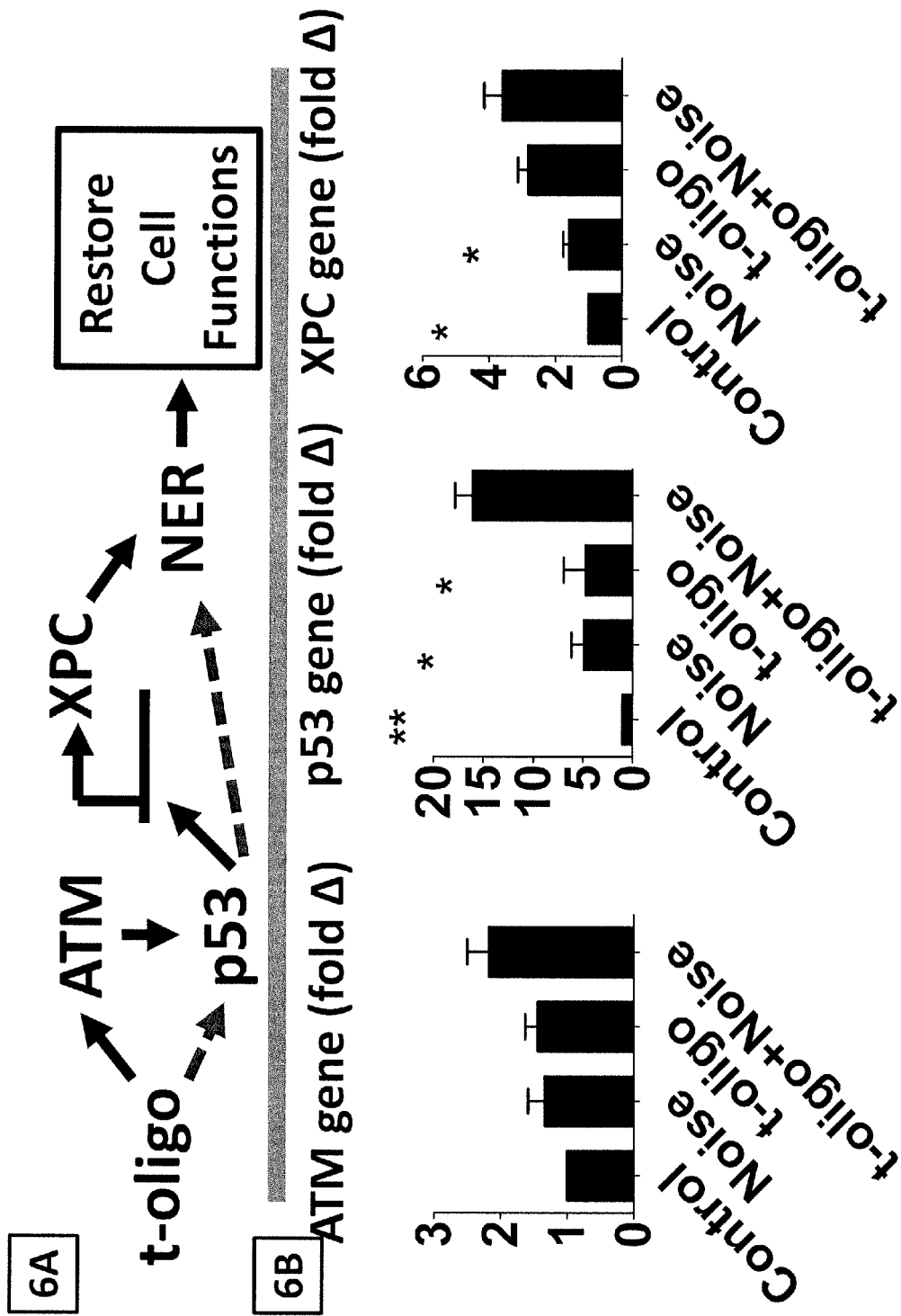

T-oligo+noise dose-response. The noise (8 kHz OBN @105/16hrs) is held constant while t-oligo dose is varied. All data are 24 hrs after the noise exposure T-oligo+noise time course. The noise (8 kHz OBN @105/16hrs) and t-oligo (18 mg/ml) is held constant while the time of harvest/flash frozen varied.

METHODS OF TREATING, INHIBITING AND/OR PREVENTING AN AUDITORY IMPAIRMENT

The subject application claims the priority of U.S. Ser. No. 62/300,585, filed Feb. 26, 2016, the disclosure of which, in its entirety, is hereby incorporated by reference into this application.

This invention was made with government support by the United States Department of Veterans Affairs. The government has certain rights in the invention.

Throughout this application various publications are referenced. The disclosures of these publications in their entireties are hereby incorporated by reference into this application in order to more fully describe the state of the art to which this invention pertains.

FIELD OF THE INVENTION

The present invention relates to the diagnostic and therapeutic uses of oligonuclucleotides for treating, inhibiting and/or preventing auditory impairments.

BACKGROUND OF THE INVENTION

For people who suffer from auditory impairments, it can be difficult to adjust to loss of hearing because hearing has been an essential aspect of their communication and relationships. New treatments that alleviate or inhibit auditory impairments are needed. The invention provides a novel therapy to alleviate auditory impairments.

SUMMARY OF THE INVENTION

The invention provides methods for treating, inhibiting and/or preventing auditory impairments associated with outer hair cells of the cochlea in a subject. In one embodiment, the method comprises administering to the subject an effective amount of a composition comprising, as an active agent, an oligonucleotide sequence having a portion of a mammalian telomere sequence thereby treating, inhibiting and/or preventing the auditory impairment in the subject.

An article of manufacture and a kit comprising a composition comprising, as an active agent, an oligonucleotide sequence having a portion of a mammalian telomere sequence are also provided.

BRIEF DESCRIPTION OF THE DRAWINGS

FIG. 2A-2D. Recovery of outer hair cell function with t-oligo treatment in an experimental research design (n=6). Panels 2A and 2B are outer hair cell responses measured with the $2f_1-f_2$ distortion product otoacoustic emissions while panels 2C and 2D are outer hair cell responses measured with the $2f_2-f_1$ distortion product otoacoustic emissions. Baseline (black circle) and biological and instrumental noise floor (solid gray line) measurements were performed prior to exposure to damaging noise dose (105 dB SPL for 16 hours) at 5.6 to 11.5 kHz (vertical gray bar). Within 24 hours after the noise exposure, the left ears received saline (vehicle control) via transtympanic injection while the right ears received t-oligo via transtympanic injection. Follow up $2f_1-f_2$ and the $2f_2-f_1$ measurements were performed at 1 week (black starts) and two months (open triangles). Each data point in all panels represent the mean data from 6 animals and the error bars are standard errors (±).

FIG. 4. Immunoblot assays of phosphorylated (activated) p53 and total p53 expressed in the cochlea.

FIG. 5. Western blot detection of phosphorylation of protein substrates with ATM/ATR/DNA-Pkc target consensus motifs (hydrophobic aa-Ser*/Thr*-hydrophilic aa) such as Leu(Ser*/Thr*)Gln (* indicates phosphorylated site).

FIG. 6A-6B. T-oligo treatment increases the expression of protective DNA repair genes in the mammalian cochlea. Panel A shows a hypothetical model to explain the protective effect of t-oligo treatment. Panel B shows that t-oligo+noise may increase ATM, p53 and XPC gene expressions.

DETAILED DESCRIPTION OF THE INVENTION

Figure 1:
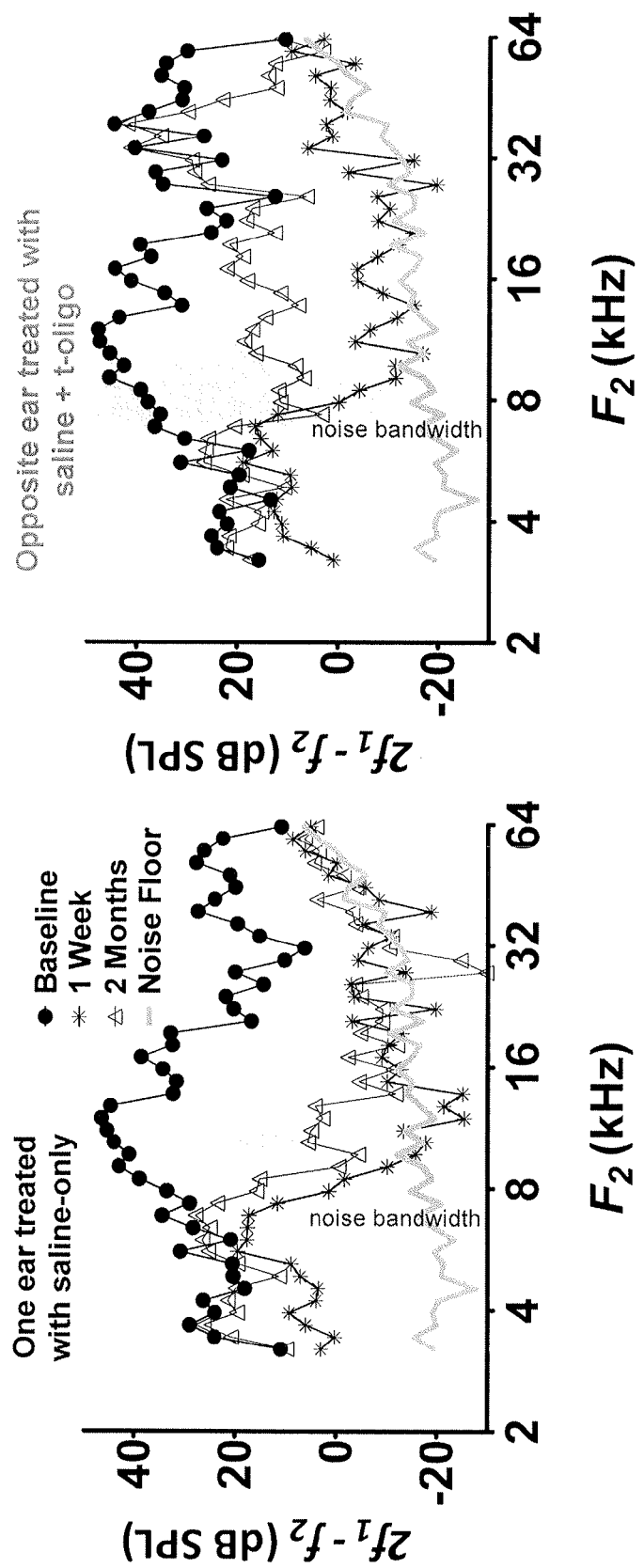
FIG. 1. Recovery of cochlear outer hair cell function with t-oligo treatment in a single subject research design. At baseline both left (left panel) and right (right panel) ear outer hair cell function was measured with the $2f_1-f_2$ distortion product otoacoustic emissions. The y-axis illustrates the level of the outer hair cell responses while the x-axis illustrates the frequency location of the cells along the basilar membrane. Note the robust response (black circles) from both ears, which are significantly elevated above the biological and instrumental noise floor (solid gray line). The animal was then exposed to a damaging noise dose (105 dB SPL for 16 hours). The vertical gray bar represents the bandwidth of the damaging noise (5.6 to 11.5 kHz). Within 24 hours after the noise exposure, the left ear received saline (vehicle control) via transtympanic injection while the right ear received t-oligo via transtympanic injection. Outer hair cell responses are measured at 1 week (black star) and 2 months (open triangle).

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which the present disclosure belongs. As used herein the following terms have the following meanings.

As used herein, the term "about" when used before a numerical designation, e.g., temperature, time, amount, concentration, and such other, including a range, indicates approximations which may vary by (+) or (−) 10%, 5% or 1%.

As used herein, the term "administration" may be effected in one dose, continuously or intermittently or by several subdoses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include intratumoral delivery, peritumoral delivery, intraperitoneal delivery, intrathecal delivery, intramuscular injection, subcutaneous injection, intravenous delivery, nasal spray and other mucosal delivery (e.g. transmucosal delivery), intra-arterial delivery, intraventricular delivery, intrasternal delivery, intracranial delivery, intradermal injection, transtympanic injection, electroincorporation (e.g., with electroporation), ultrasound, jet injector, oral, transtympanic, intracochlear and topical patches.

A "therapeutic agent," as used herein, may be a molecule, or compound that is useful in treatment of a disease or condition. A "therapeutically effective amount," "therapeutically effective concentration" or "therapeutically effective dose" is the amount of a compound that produces a desired therapeutic effect in a subject, such as preventing, inhibiting and/or treating a target condition, alleviating symptoms associated with the condition, producing a desired physiological effect, or allowing imaging or diagnosis of a condition that leads to treatment of the disease or condition. The precise therapeutically effective amount is the amount of the composition that will yield the most effective results in terms of efficacy of treatment in a given subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{(st)}$ Edition, Univ. of Sciences in Philadelphia (USIP), Lippincott Williams & Wilkins, Philadelphia, Pa., 2005.

"Treating" or "treatment" of a condition, disease or disorder may refer to preventing the condition, disease or disorder, slowing the onset or rate of development of the condition, disease or disorder, reducing the risk of developing the condition, disease or disorder, preventing or delaying the development of symptoms associated with the condition, disease or disorder, reducing or ending symptoms associated with the condition, disease or disorder, generating a complete or partial regression of the condition, disease or disorder, or some combination thereof. Examples of diseases or disorders include auditory impairments such loudness recruitment, hyperacusis, diplacusis, hearing loss due to illness or infection, temporary hearing loss, permanent hearing loss, sensory hearing loss, sensorineural hearing loss, tinnitus, medication involved or induced hearing loss (e.g., as a result of chemotherapy or radiation therapy), auditory neuropathy, auditory processing disorders (APD), central hearing loss or speech intelligibility deficits.

A "subject" is a vertebrate, preferably a mammal, more preferably a human. Mammals include, but are not limited to, farm animals (such as cows), pets (such as cats, dogs and horses), primates, mice and rats.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the compositions of the invention are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The compositions of the invention can be administered by any parenteral route, e.g., as ear drops, ear wash, ear cream, ear foam, ear ointment, in the form of a pharmaceutical formulation comprising the active ingredient, optionally in the form of a non-toxic organic, or inorganic, acid, or base, addition salt, in a pharmaceutically acceptable dosage form.

Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials. Extemporaneous injection solutions and suspensions may be prepared from sterile powders, granules and tablets of the kind previously described.

Methods of the Invention

The present invention provides, for the first time, methods of treating, inhibiting and/or preventing an auditory impairment associated with outer hair cells of the cochlea in a subject comprising administering to said subject an effective amount of a composition comprising, as an active agent, an oligonucleotide sequence having a portion of a mammalian telomere sequence so as to reduce the auditory impairment thereby treating, inhibiting and/or preventing the auditory impairment in the subject.

The invention further provides methods for preventing auditory impairment in a subject comprising administering to the subject an effective amount of a composition comprising, as an active agent, an oligonucleotide with a 3' overhang sequence of a mammalian telomere or a portion thereof or a variant thereof. In one embodiment, the composition comprises an oligonucleotide for treating, inhibiting and/or preventing auditory impairment, a second active agent for treating, inhibiting and/or preventing auditory impairment and a pharmaceutically acceptable carrier.

The invention further provides methods for preventing loss of cochlear outer hair cell function in a subject comprising administering to said subject an effective amount of a composition comprising, as an active agent, an oligonucleotide sequence having a portion of a mammalian telomere sequence or a variant of a mammalian telomere sequence, thereby preventing loss of cochlear outer hair cell function. In an embodiment, the loss of cochlear outer hair cell function in a subject may be associated with noise induced hearing loss (NIHL), physical trauma, metabolic stress, temperature stress, hypoxia, chemical ototoxicant and/or presbycusis. In another embodiment, the loss of cochlear outer hair cell function in a subject is associated with noise induced hearing loss (NIHL). In another embodiment, the loss of cochlear outer hair cell function in a subject is associated with noise trauma. In yet another embodiment, the noise induced hearing loss (NIHL), physical trauma, metabolic stress, temperature stress, hypoxia, chemical ototoxicant and/or presbycusis results in DNA damage. In yet another embodiment, the noise trauma results in DNA damage. In a further embodiment, the DNA damage is oxidative DNA damage.

In one embodiment, the composition is administered prior to damage or insult to cochlear outer hair cell required for loss of cochlear outer hair cell function. In another embodiment, the composition is administered at the time of damage or insult to cochlear outer hair cell required for loss of cochlear outer hair cell function. In yet another embodiment, the composition is administered shortly after damage or insult to cochlear outer hair cell required for loss of cochlear outer hair cell function.

In one embodiment, the composition is administered once. In another embodiment, the composition is administered repeatedly.

Further, the oligonucleotide may increase p53 activity. In one embodiment, the p53 activity is increased without an increase in total p53 protein level sufficient to induce apoptosis. In another embodiment, the p53 activity is increased with a decrease in total p53 protein level.

Further, the oligonucleotide may increase activity of DNA repair protein. In one embodiment, the DNA repair protein is selected from the group consisting of XPC, XPF and XPG proteins.

Further, the oligonucleotide may increase nucleotide excision repair (NER). In one embodiment, the nucleotide excision repair (NER) is mediated by DNA repair protein.

Further, the oligonucleotide may increase pro-cell survival protein. In one embodiment, the pro-cell survival protein is XPC.

In one embodiment, preventing loss of cochlear outer hair cell function in a subject comprises survival of cochlear outer hair cells. In another embodiment, preventing loss of cochlear outer hair cell function comprises reduced loss of measure distortion product optoacoustic emission (DPOAE) response following damage or insult to cochlear outer hair cell. In yet another embodiment, preventing loss of cochlear outer hair cell function comprises reduced or continued maintenance of auditory brain stem response following damage or insult to outer hair cell. In a further embodiment, damage or insult to outer hair cell is selected from the group consisting of noise induced hearing loss (NIHL), physical trauma, metabolic stress, temperature stress, hypoxia, chemical ototoxicant and presbycusis. In an embodiment, damage or insult to outer hair cell comprises noise trauma. In yet a further embodiment, damage or insult to outer hair cell comprises noise induced hearing loss (NIHL).

The invention further provides methods for restoring cochlear outer hair cell function in a subject comprising administering to said subject an effective amount of a composition comprising, as an active agent, an oligonucleotide sequence having a portion of a mammalian telomere sequence or a variant of a mammalian telomere sequence so as to increase the transcription of ATM, p53, XPC, XPF and XPG genes, thereby restoring cochlear outer hair cell function.

In one embodiment, increased transcription is observed at 24 hours after administration of the oligonucleotide. In another embodiment, the increased transcription observed at 24 hours does not result in a change in p53 protein concentration or activity such as to induce apoptosis of cochlear outer hair cell. In yet another embodiment, the increased transcription observed at 24 hours after administration of the oligonucleotide is maintained for ATM, XPF and XPG genes at 48 hours and 72 hours relative to p53 and XPC genes. In a further embodiment, transcription of p53 and XPC genes at 48 hours and 72 hours after administration of the oligonucleotide is decreased relative to the transcription observed at 24 hours after administration of the oligonucleotide.

The invention further provides methods for treating, inhibiting and/or preventing an auditory impairment in a subject wherein treating an auditory impairment causes recovery of cochlear function, brainstem function or both cochlear and brainstem function.

Examples of recovery of cochlear function include, but are not limited to, a greater or more rapid improvement in distortion product optoacoustic emission observed following administration of the oligonucleotide than in its absence.

Examples of recovery of brainstem function include, but are not limited to, a greater or more rapid improvement in auditory brainstem response, pure-tone hearing test, or a combination thereof, than in its absence.

The invention further provides methods for treating, inhibiting and/or preventing an auditory impairment associated with outer hair cells of the cochlea in a subject. For example, treating an auditory impairment associated with outer hair cells of the cochlea in a subject comprises increasing repair of damaged DNA in the outer hair cells.

Examples of recovery associated with outer hair cells of the cochlea include, but are not limited to, recovery or preservation of retrocochlear function, and recovery of outer hair cell function.

Examples of auditory impairments include, but are not limited to, temporary hearing loss, permanent hearing loss, sensory hearing loss, sensorineural hearing loss, tinnitus, loudness recruitment, hyperacusis, diplacusis and speech intelligibility deficits.

Further, the auditory impairment in the subject may be due to noise injury, environmental toxin, toxic drug, mutagen, chemotherapeutic agent, aging, diabetes, diabetes-related complications, infection, cancer, antibiotics, drug treatment, treatment for infection, or cancer therapy.

In an embodiment, the auditory impairment may be associated with noise induced hearing loss (NIHL), physical trauma, metabolic stress, temperature stress, hypoxia, chemical ototoxicant and/or presbycusis. In another embodiment, the auditory impairment is associated with noise trauma. In another embodiment, the auditory impairment is noise induced hearing loss (NIHL). In a further embodiment, the noise induced hearing loss (NIHL), physical trauma, metabolic stress, temperature stress, hypoxia, chemical ototoxicant and/or presbycusis or noise trauma results in DNA damage. In another embodiment, the noise trauma results in DNA damage. In yet a further embodiment, the DNA damage is mediated by reactive oxygen species (ROS).

In other embodiments, the auditory impairment may be associated with damage, dysfunction or loss of cochlear outer hair cell, cochlear inner hair cell, cochlear sensory epithelium, cochlear non-sensory epithelium, stria vascularis, spiral ligament, spiral limbus, cochlear supporting cell, cochlear stem cell, hearing-related stem cell, sensorineural cell, hearing-associated neuron, auditory nerve, pre-synaptic sensory function or post-synaptic neural function. For example, the pre-synaptic sensory function may be a function associated with cochlear outer hair cell or cochlear inner hair cell. In yet another example, the post-synaptic neural function may be a function associated with an auditory nerve.

In yet another embodiment, the auditory impairment associated with outer hair cells of the cochlea in a subject comprises a compromised or depressed distortion product optoacoustic emission (DPOAE) of the outer hair cells. In another embodiment, the auditory impairment associated with outer hair cells of the cochlea in a subject comprises impairment of retrocochlear function, wherein the retrocochlear function is assessed as an auditory brainstem response.

In one embodiment of the invention, the composition increases activation of p53 but lowers the total amount of p53. For example, increasing activation of p53 results in increased phosphorylation of p53. In another example, increased phosphorylation or activation of p53 protein results in increased expression of DNA repair genes. In another example, increasing activation of the p53 gene restores cochlear cell function.

In one embodiment of the invention, increased expression of DNA repair genes is associated with increased activity of DNA repair proteins. In a further embodiment, increased activity of DNA repair protein(s) results in repair of DNA damage in cochlear outer hair cells.

In one embodiment of the invention, the composition increases global DNA damage signaling in the cochlea. Increased global DNA damage signaling in the cochlea comprises increased protein kinase activity of ATM/ATR/DNA-PK family of protein kinases.

In an embodiment of the invention, the portion of the mammalian telomere is located at the 3' end of the oligonucleotide sequence. In another embodiment, the portion of the mammalian telomere is located at the 5' end of the oligonucleotide sequence.

"Oligonucleotide sequence" as used herein, generally refers to short polynucleotides that are generally, but not necessarily, less than about 50 nucleotides in length. For example, the oligonucleotide sequence of the composition may comprise a range of between a 2-base oligonucleotide sequence to 21-base oligonucleotide sequence. Merely by way of example, in one embodiment, the oligonucleotide sequence in the composition comprises a range of between 11-base oligonucleotide sequence to 21-base oligonucleotide sequence. In a further embodiment, the oligonucleotide sequence comprises a range of between 8-base oligonucleotide sequence to 21-base oligonucleotide sequence. In yet a further embodiment, the oligonucleotide sequence comprises an 11-base oligonucleotide sequence. For example, the 11-base oligonucleotide sequence based on a 5'-3' direction, may be GTTAGGGTTAG.

In still a further embodiment, the oligonucleotide sequence may contain or consist of a 2-base oligonucleotide sequence. For example, the 2-base oligonucleotide sequence may be TT.

Further, the invention provides an embodiment wherein the portion of the mammalian telomere at the 3' end is a 3' overhang sequence having any of the sequence TAGGGT, AGGGTT, GGGTTA, GGTTAG, and GTTAGG, or repeats thereof.

Suitable oligonucleotide sequences may be at least about 70% identical, preferably at least about 80% identical, more preferably at least about 90% identical and most preferably at least about 95% identical (e.g., 95%, 96%, 97%, 98%, 99%, 100%) to the reference oligonucleotide sequences of the present invention (i.e., see examples herein). Largest match between the respective sequences over the entire length of the respective reference sequence is performed. Similarly, when the comparison is performed by a BLAST algorithm (for longer sequences), the parameters of the algorithm are selected to give the largest match between the respective sequences over the entire length of the respective reference sequence(s).

Homology is determined by aligning the variant sequence against the reference sequence and calculating the largest percent identity of the variant sequence to the reference sequence. The homology is further determined using a computer algorithm. The computer algorithm comprises a pairwise comparison of one nucleotide sequence against a second nucleotide sequence. In one embodiment, the alignment introduces no gap in the nucleotide sequence of either the variant or the reference sequence. In another embodiment, the alignment introduces one or more gaps so as to obtain maximal matches between the two aligned sequences but no more than one gap for every 10 bases so as to maximize percent identity.

In accordance with the practice of the invention, the oligonucleotide sequence may be isolated from a telomere, recombinantly made or chemically synthesized. In one embodiment of the invention, the oligonucleotide is a deoxyoligonucleotide. In another embodiment, the oligonucleotide is a phosphorylated oligonucleotide. For example, the phosphorylated oligonucleotide may have a phosphate group at C-5' position of 5' terminal deoxyribose. In another embodiment, the oligonucleotide may lack a phosphate group at C-5' position of 5' terminal deoxyribose.

In accordance with the practice of the invention, the oligonucleotide may be a modified oligonucleotide. For example, the modified oligonucleotide may comprise a modified phosphodiester backbone, modified nucleoside, modified base, modified sugar or a combination thereof.

Modified phosphodiester backbones may include any of a phosphorothioate, methylphosphonate, inverted 5'-5' linkage, inverted 3'-3' linkage, biotin-modified on the 5' end, biotin-modified on the 3' end, or N-(2-aminoethyl)-glycine repeat units linked by peptide bonds.

Modified nucleosides may include any of 2'-fluoro adenosine, 2'-fluoro deoxyguanosine, 2'-fluoro deoxyuridine, 2'-O methyl adenosine, 2'-O methyl guanosine, 2'-O methyl uridine, 5-bromouridine, propyne deoxyuridine, or biotin-modified nucleoside.

Modified bases may include any of a thymine dimer, biotin-modified thymine, and biotin-modified base. Suitable examples of modified sugars include, but are not limited to, L-ribose, D-ribose, L-deoxyribose, dideoxyribose, and biotin-modified sugar.

The oligonucleotide sequence of the composition may be a sequence which is guanine-rich and forms a quadruplex secondary structure. For example, the quadruplex secondary structure may be formed within a single oligonucleotide or between two or more oligonucleotides. In another example, the quadruplex secondary structure may facilitate uptake of the oligonucleotide sequence into a cell, be resistant to degradation by nucleases, and/or permit accumulation of the oligonucleotide in the nucleus.

In accordance with the practice of the invention, the composition of the invention may be administered topically, by injection, as a swab, as a patch, as a droplet, as a stream, as an aerosol, by an implant, by a device generating a voltage potential, by a nanoparticle, by a projectile, in an aqueous solution, in saline solution, in a non-aqueous solution, in glycerol, as a solid, as a fluid, as a micelle, as a salt, as a complex with a metal, as a complex with a counter ion, as a complex with a lipid, or as a conjugate with a cell targeting agent. In an embodiment of the invention, the composition is administered to the cochlea. In a further embodiment of the invention, administration to the cochlea is a transtympanic injection or intratympanic injection. In an embodiment of the invention wherein the composition is administered through a tympanostomy tube or ear tube. In a further embodiment of the invention, the administration through the tympanostomy tube or ear tube utilizes a pump or positive pressure.

Compositions

The invention provides a pharmaceutical composition comprising, as an active agent, an oligonucleotide sequence having a portion of a mammalian telomere sequence and, optionally, a suitable carrier.

Further, the composition may additionally comprise a second active agent for treating, inhibiting and/or preventing auditory impairment, wherein the second active agent promotes survival of cochlear outer hair cells.

Further, the composition may additionally comprise a second active agent selected from the group consisting of antioxidant, growth factor, calcium channel inhibitor/blocker, calcium antagonist, calcium chelator, calcineurin inhibitor, glutamate antagonist, vasodilator, steroid, c-Jun-N-terminal kinase (JNK) inhibitor, Src protein tyrosine kinase (Src-PTK) inhibitor, vitamin, nootropics, energy enhancer, caspase inhibitor, calpain inhibitor, iron chelator and inducer of heat shock proteins. Beneficial effect of these second active agents along with their mode of action may be found in Oishi & Schacht, 2011 (Oishi N, Schacht J. Emerging treatments for noise-induced hearing loss. Expert Opin Emerg Drugs. 2011 June; 16(2):235-45. doi: 10.1517/14728214.2011.552427. Epub 2011 Jan. 20. Review. PubMed PMID: 21247358; PubMed Central PMCID: PMC3102156), Ohlemiller, 2008 (Ohlemiller K K. Recent findings and emerging questions in cochlear noise injury. Hear Res. 2008 November; 245(1-2):5-17. doi: 10.1016/j.heares.2008.08.007. Epub 2008 Aug. 29. Review. PubMed PMID: 18790034; PubMed Central PMCID: PMC2610263) and Le Prell et al., 2007 (Le Prell C G, Yamashita D, Minami S B, Yamasoba T, Miller J M. Mechanisms of noise-induced hearing loss indicate multiple methods of prevention. Hear Res. 2007 April; 226(1-2):22-43. Epub 2006 Dec. 4. Review. PubMed PMID: 17141991; PubMed Central PMCID: PMC1995566).

Further, the oligonucleotide has a sequence comprising a portion of a mammalian telomere sequence or a variant of a mammalian telomere sequence. In one embodiment, the mammalian telomere sequence is a direct repeat of a hexanucleotide TTAGGG, which may be described as $(TTAGGG)_n$, wherein "n" is the number of TTAGGG repeats.

The antioxidant may be selected from the group consisting of glutathione (GSH), GSH/glutathione monoethyl ester (GSHE), D-methionine, ebselen, resveratrol, ascorbic acid, water-soluble coenzyme Q10, salicylate, trolox, ferulic acid, N-acetylcysteine (NAC), idebenone, edaravone, hydroxyphenyl-N-tert-butylnitrone, T-817MA, BN 82270, 2-oxothiazolidine-4-carboxylate (OTC), allopurinol, superoxide dismutase-polyethylene glycol, U74389F, R-phenylisopropyladenosine (R-PIA), mannitol and tempol.

The growth factor may be selected from the group consisting of neutrophic factor, glial cell line-derived neurotrophic factor (GDNF), insulin-like growth factor-1, brain-derived neurotrophic factor (BDNF), basic fibroblast growth factor (bFGF or FGF2), acidic fibroblast growth factor (aFGF or FGF1), neurotrophin-3 (NT3), nerve growth factor (NGF) and neurotrophin-4/5 and ciliary neurotrophic factor (CNTF).

The calcium channel inhibitor/blocker may be selected from the group consisting of trimethadione, ethosuximide and amitriptyline.

The calcineurin inhibitor may be selected from the group consisting of FK506 and cyclosporin A.

The glutamate antagonist may be selected from the group consisting of NMDA receptor antagonist MK-801 and caroverine.

The vasodilator may be selected from the group consisting of 8-iso-PGF2alpha antagonist, SQ29548, $Mg^{2+}$, betahistine, hydroxyethyl starch (HES), HES 70 and HES 200.

The steroid may be selected from the group consisting of glucocorticoid, corticosteroid, dexamethasone, prednisolone, dehydroepiandrosterone, estradiol and ERP-selective agonist 2,3-bis(4-hydroxyphenyl)-proprionitrile.

The c-Jun-N-terminal kinase (JNK) inhibitor may be selected from the group consisting of retinoic acid, AM-111, XG-102 peptide, D-JNKI-1 peptide, CEP-1347 and CEP-11004.

The Src protein tyrosine kinase (Src-PTK) inhibitor may be selected from the group consisting of KX1-004, KX1-005 and KX1-174.

The vitamin may be selected from the group consisting of ascorbic acid, vitamin B12, vitamin E and vitamin A.

The nootropics may be selected from the group consisting of piracetam, oxiracetam and aniracetam.

The energy enhancer may be selected from the group consisting of acetyl-L-carnitine (ALCAR), creatine and ATP.

The caspase inhibitor may be selected from the group consisting of z-VAD-FMK, z-WEHD-FMK, z-VDVAD-FMK, z-DEVD-FMK (CAS No.: 210344-95-9), z-YVAD-FMK, z-VEID-FMK, z-IETD-FMK, z-LEHD-FMK, z-AEVD-FMK, z-LEED-FMK, z-FA-FMK, z-VKD-FMK, AZ 10417808, IDN-6556, IDN-8066, IDN-7503, IDN-7436, IDN-1965, IDN-5370, IDN-7866, M867, compound 34, emricasan, pralnacasan, belnacasan, wedelolactone, z-Asp-2,6-dichlorobenzoyloxymethylketone, PKR inhibitor, Boc-Asp(OMe)-fluoromethyl ketone, ivachtin, gly-phe beta-naphthylamide, 5-[(S)-(+)-2-(Methoxymethyl)pyrrolidino]sulfonylisatin (CAS No.: 220509-74-0), BI-9B12 (CAS No.: 848782-29-6), Ac-YVAD-CMK (CAS No.: 178603-78-6), Ac-Tyr-Val-Ala-Asp-2,6-dimethylbenzoyloxymethyl ketone, caspase-3 inhibitor III (CAS No.: 285570-60-7), Ac-LEHD-CMK (CAS No.: 403848-57-7), Ac-VAD-cho, Ac-AAVALLPAVLLALLAPYVAD-CHO, Ac-YVAD-cho (CAS No.: 143313-51-3), Z-YVAD(OMe)-FMK, Ac-DEVD-cho, Ac-AAVALLPAVLLALLAPDEVD-CHO, Ac-AAVALLPAVLLALLAPLEVD-CHO, Ac-LEVD-cho, Ac-VEID-FMK, Ac-IETD-CHO (CAS No.: 191338-86-0), Z-Leu-Glu(OMe)-His-Asp(OMe)-Fluoromethylketone, Z-VAD(OH)-FMK (CAS No.: 634911-81-2), Z-VAD(OMe)-FMK (CAS No.: 187389-52-2), NSCI, DICA, Q-VD-OPh, crmA, p35, p49 and XIAP.

The calpain inhibitor may be selected from the group consisting of leupeptin, aclacinomycin A (CAS No.: 57576-44-0), Ac-LLM-CHO (CAS No.: 136632-32-1), E-64 (CAS No.: 66701-25-5), E-64-c (CAS No.: 76684-89-4), MDL-28170 (CAS No.: 88191-84-8), calpeptin (CAS No.: 117591-20-5), ALLN (CAS No.: 110044-82-1), PD 150606 (CAS No.: 179528-45-1), calpain inhibitor I (CAS No.: 110044-82-1), calpain inhibitor VI (CAS No.: 190274-53-4), leupeptin hemisulfate (CAS No.: 103476-89-7), calpain inhibitor XII, penicillide (CAS No.: 55303-92-9), MDL 28170 (CAS No.: 88191-84-8), MG-132 (CAS No.: 133407-82-6), MG 202 (CAS No.: 110044-82-1) and human acetylcalpastatin (184-210) (CAS No.: 123714-50-1).

The iron chelator may be selected from the group consisting of deferoxamine mesylate (DFO), 3-aminopyridine-2-carboxaldehyde thiosemicarbazone (CAS No.: 236392-56-6), 2-furildioxime, enterobactin8-hydroxyquinoline-2-carboxylic acid, deferiprone, deferasirox and deferoxamine (Desferal®).

The inducer of heat shock proteins is selected from the group consisting of geranylferanyl-acetone, geranylgeranylacetone (GGA), shikonin, Tex-OE® and 2-cyclopenten-1-one.

The oligonucleotide sequence generally refers to short polynucleotides that are generally, but not necessarily, less than about 50 nucleotides in length. For example, the oligonucleotide sequence of the composition may comprise a range of between a 2-base oligonucleotide sequence to 21-base oligonucleotide sequence. Merely by way of example, in one embodiment, the oligonucleotide sequence in the composition comprises a range of between 11-base oligonucleotide sequence to 21-base oligonucleotide sequence. In a further embodiment, the oligonucleotide sequence comprises a range of between 8-base oligonucleotide sequence to 21-base oligonucleotide sequence. In yet a further embodiment, the oligonucleotide sequence comprises an 11-base oligonucleotide sequence.

For example, the 11-base oligonucleotide sequence based on a 5'-3' direction, may be GTTAGGGTTAG (SEQ ID NO: 1). In a further example, the 11-base oligonucleotide sequence is 100% homologous to a mammalian telomere sequence.

In a further embodiment, the oligonucleotide sequence may contain or consist of a 20-base oligonucleotide sequence. For example, the 20-base oligonucleotide sequence comprises GGTTGGTTGGTTGGTTGGTT (SEQ ID NO: 2) and wherein the 20-base oligonucleotide sequence is a variant with 50% homology to a mammalian telomere sequence comprising direct repeats of a hexanucloetide sequence (TTAGGG). In yet another example, the 20-base oligonucleotide sequence comprises CCTTGGTTGGTTGGTTGGTT (SEQ ID NO: 3) and wherein the 20-base oligonucleotide sequence is a variant with 40% homology to a mammalian telomere sequence comprising direct repeats of a hexanucleotide sequence (TTAGGG).

In yet a further embodiment, the oligonucleotide sequence may comprise a range of between a 9-base oligonucleotide sequence to a 20-base oligonucleotide sequence.

In a further embodiment, the oligonucleotide sequence may contain or consist of a 9-base oligonucleotide sequence. For example, the 9-base oligonucleotide sequence comprises GTTAGGGTT, TTAGGGTTA, GGGTTAGGG, or GTTAGGGTTAGGGTTA (SEQ ID NO: 4) and wherein the 9-base oligonucleotide sequence is 100% homologous to a mammalian telomere sequence. In yet another example, the 9-base oligonucleotide sequence comprises GAGTATGAG and wherein the 9-base oligonucleotide sequence is a variant with 44% homology to a mammalian telomere sequence comprising direct repeats of a hexanucleotide sequence (TTAGGG).

In a further embodiment, the oligonucleotide sequence may contain or consist of a 15-base oligonucleotide sequence. For example, the 15-base oligonucleotide sequence comprises GTTAGGGTTAGGGTT (SEQ ID NO: 5) and wherein the 15-base oligonucleotide sequence is 100% homologous to a mammalian telomere sequence. In another example, the 15-base oligonucleotide sequence comprises GTTAGGTTTAAGGTT (SEQ ID NO: 6), GGTAGGTGTAGGGTG (SEQ ID NO: 7), GGTAGGTGTAGGATT (SEQ ID NO: 8) or GGTAGGTGTAGGGTG (SEQ ID NO: 7), and wherein the 15-base oligonucleotide sequence is a variant with 87%, 73% or 75% homology to a mammalian telomere sequence comprising direct repeats of a hexanucleotide sequence (TTAGGG), respectively.

In yet another embodiment, the oligonucleotide sequence may contain or consist of a 16-base oligonucleotide sequence. For example, the 16-base oligonucleotide sequence comprises GTTAGGGTTAGGGTTA (SEQ ID NO: 4) and wherein the 16-base oligonucleotide sequence is 100% homologous to a mammalian telomere sequence. In another example, the 16-base oligonucleotide sequence comprises GATAAGGGATTGGGAT (SEQ ID NO: 9), GGTAGGTGTAGGATTT (SEQ ID NO: 10), GGTTAGGTGTAGGTTT (SEQ ID NO: 11), GGTTAGGTGGAGGTTT (SEQ ID NO: 12), GGTTAGGTTTAGGTTT (SEQ ID NO:

13), GGTTAGGTTAAGGTTA (SEQ ID NO: 14), GTTAGGGTTAGGGTTA (SEQ ID NO: 4), or GGTTGGT-TGGTTGGTT (SEQ ID NO: 15) and wherein the 16-base oligonucleotide sequence is a variant with 44%, 69%, 81%, 75%, 88%, or 56% homology to a mammalian telomere sequence comprising direct repeats of a hexanucleotide sequence (TTAGGG), respectively.

In still a further embodiment, the oligonucleotide sequence may contain or consist of a 2-base oligonucleotide sequence. For example, the 2-base oligonucleotide sequence may be TT.

The 2-base oligonucleotide sequence may be derived from a mammalian telomere sequence comprising direct repeats of a hexanucleotide sequence (TTAGGG). The 2-base oligonucleotide sequence derived from a mammalian telomere sequence may be selected from the group comprising TT, TA, AG, GG and GT.

Merely by way of example, in one embodiment, the length of the oligonucleotide is less than 100 bases. In a further embodiment, the length of the oligonucleotide is longer than 2 bases. In yet another embodiment, the length of the oligonucleotide is between 2 and 100 bases, 2 and 50 bases, 2 and 30 bases, 9 and 21 bases and/or 2 and 21 bases. In yet a further embodiment, the oligonucleotide is selected from the group consisting of 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases and 30 bases.

In further embodiments, the oligonucleotide with 2 bases is selected from the group consisting of TT, TA, AG, GG and GT. The oligonucleotide with 3 bases is selected from the group consisting of TTA, TAG, AGG, GGG, GGT and GTT. The oligonucleotide with 4 bases is selected from the group consisting of TTAG, TAGG, AGGG, GGGT, GGTT and GTTA. The oligonucleotide with 5 bases is selected from the group consisting of TTAGG, TAGGG, AGGGT, GGGTT, GGTTA and GTTAG. The oligonucleotide with 6 bases is selected from the group consisting of TTAGGG, TAGGGT, AGGGTT, GGGTTA, GGTTAG and GTTAGG. The oligonucleotide with 7 bases is selected from the group consisting of TTAGGGT, TAGGGTT, AGGGTTA, GGGTTAG, GGT-TAGG and GTTAGGGT. The oligonucleotide with 8 bases is selected from the group consisting of TTAGGGTT, TAGGGTTA, AGGGTTAG, GGGTTAGG, GGTTAGGG and GTTAGGGT. The oligonucleotide with 9 bases is selected from the group consisting of TTAGGGTTA, TAGGGTTAG, AGGGTTAGG, GGGTTAGGG, GGT-TAGGGT and GTTAGGGTT. The oligonucleotide with 10 bases is selected from the group consisting of TTAGGGT-TAG (SEQ ID NO: 16), TAGGGTTAGG (SEQ ID NO: 17), AGGGTTAGGG (SEQ ID NO: 18), GGGTTAGGGT (SEQ ID NO: 19), GGTTAGGGTT (SEQ ID NO: 20) and GTTAGGGTTA (SEQ ID NO: 21). The oligonucleotide with 11 bases is selected from the group consisting of TTAGGGTTAGG (SEQ ID NO: 22), TAGGGTTAGGG (SEQ ID NO: 23), AGGGTTAGGGT (SEQ ID NO:24), GGGTTAGGGTT (SEQ ID NO: 25), GGTTAGGGTTA (SEQ ID NO: 26) and GTTAGGGTTAG (SEQ ID NO: 1). The oligonucleotide with 12 bases is selected from the group consisting of TTAGGGTTAGGG (SEQ ID NO: 27), TAGGGTTAGGGT (SEQ ID NO: 28), AGGGTTAGGGTT (SEQ ID NO: 29), GGGTTAGGGTTA (SEQ ID NO: 30), GGTTAGGGTTAG (SEQ ID NO: 31) and GTTAGGGT-TAGG (SEQ ID NO: 32). The oligonucleotide with 13 bases is selected from the group consisting of TTAGGGT-TAGGGT (SEQ ID NO: 33), TAGGGTTAGGGTT (SEQ ID NO: 34), AGGGTTAGGGTTA (SEQ ID NO: 35), GGGT-TAGGGTTAG (SEQ ID NO: 36), GGTTAGGGTTAGG (SEQ ID NO: 37) and GTTAGGGTTAGGG (SEQ ID NO: 38). The oligonucleotide with 14 bases is selected from the group consisting of TTAGGGTTAGGGTT (SEQ ID NO: 39), TAGGGTTAGGGTTA (SEQ ID NO: 40), AGGGT-TAGGGTTAG (SEQ ID NO: 41), GGGTTAGGGTTAGG (SEQ ID NO: 42), GGTTAGGGTTAGGG (SEQ ID NO: 43) and GTTAGGGTTAGGGT (SEQ ID NO: 44). The oligonucleotide with 15 bases is selected from the group consisting of TTAGGGTTAGGGTTA (SEQ ID NO: 45), TAGGGTTAGGGTTAG (SEQ ID NO: 46), AGGGT-TAGGGTTAGG (SEQ ID NO: 47), GGGTTAGGGT-TAGGG (SEQ ID NO: 48), GGTTAGGGTTAGGGT (SEQ ID NO: 49) and GTTAGGGTTAGGGTT (SEQ ID NO: 5). The oligonucleotide with 16 bases is selected from the group consisting of TTAGGGTTAGGGTTAG (SEQ ID NO: 50), TAGGGTTAGGGTTAGG (SEQ ID NO: 51), AGGGT-TAGGGTTAGGG (SEQ ID NO: 52), GGGTTAGGGT-TAGGGT (SEQ ID NO: 53), GGTTAGGGTTAGGGTT (SEQ ID NO: 54) and GTTAGGGTTAGGGTTA (SEQ ID NO: 4). The oligonucleotide with 17 bases is selected from the group consisting of TTAGGGTTAGGGTTAGG (SEQ ID NO: 55), TAGGGTTAGGGTTAGGG (SEQ ID NO: 56), AGGGTTAGGGTTAGGGT (SEQ ID NO: 57), GGGT-TAGGGTTAGGGTT (SEQ ID NO: 58), GGTTAGGGT-TAGGGTTA (SEQ ID NO: 59) and GTTAGGGTTAGGGT-TAG (SEQ ID NO: 60). The oligonucleotide with 18 bases is selected from the group consisting of TTAGGGT-TAGGGTTAGGG (SEQ ID NO: 61), TAGGGTTAGGGT-TAGGGT (SEQ ID NO: 62), AGGGTTAGGGTTAGGGTT (SEQ ID NO: 63), GGGTTAGGGTTAGGGTTA (SEQ ID NO: 64), GGTTAGGGTTAGGGTTAG (SEQ ID NO: 65) and GTTAGGGTTAGGGTTAGG (SEQ ID NO: 66). The oligonucleotide with 19 bases is selected from the group consisting of TTAGGGTTAGGGTTAGGGT (SEQ ID NO: 67), TAGGGTTAGGGTTAGGGTT (SEQ ID NO: 68), AGGGTTAGGGTTAGGGTTA (SEQ ID NO: 69), GGGT-TAGGGTTAGGGTTAG (SEQ ID NO: 70), GGTTAGGGT-TAGGGTTAGG (SEQ ID NO: 71) and GTTAGGGT-TAGGGTTAGGG (SEQ ID NO: 72). The oligonucleotide with 20 bases is selected from the group consisting of TTAGGGTTAGGGTTAGGGTT (SEQ ID NO: 73), TAGGGTTAGGGTTAGGGTTA (SEQ ID NO: 74), AGGGTTAGGGTTAGGGTTAG (SEQ ID NO: 75), GGGTTAGGGTTAGGGTTAGG (SEQ ID NO: 76), GGT-TAGGGTTAGGGTTAGGG (SEQ ID NO: 77) and GTTAGGGTTAGGGTTAGGGT (SEQ ID NO: 78). The oligonucleotide with 21 bases is selected from the group consisting of TTAGGGTTAGGGTTAGGGTTA (SEQ ID NO: 79), TAGGGTTAGGGTTAGGGTTAG (SEQ ID NO: 80), AGGGTTAGGGTTAGGGTTAGG (SEQ ID NO: 81), GGGTTAGGGTTAGGGTTAGGG (SEQ ID NO: 82), GGTTAGGGTTAGGGTTAGGGT (SEQ ID NO: 83) and GTTAGGGTTAGGGTTAGGGTT (SEQ ID NO: 84). The oligonucleotide with 22 bases is selected from the group consisting of TTAGGGTTAGGGTTAGGGTTAG (SEQ ID NO: 85), TAGGGTTAGGGTTAGGGTTAGG (SEQ ID NO: 86), AGGGTTAGGGTTAGGGTTAGGG (SEQ ID NO: 87), GGGTTAGGGTTAGGGTTAGGGT (SEQ ID NO: 88), GGTTAGGGTTAGGGTTAGGGTT (SEQ ID NO: 89) and GTTAGGGTTAGGGTTAGGGTTA (SEQ ID NO: 90). The oligonucleotide with 23 bases is selected from the group consisting of TTAGGGTTAGGGTTAGGGT-TAGG (SEQ ID NO: 91), TAGGGTTAGGGTTAGGGT-TAGGG (SEQ ID NO: 92), AGGGTTAGGGTTAGGGT- TAGGGT (SEQ ID NO: 93), GGGTTAGGGTTAGGGTTAGGGTT (SEQ ID NO: 94), GGTTAGGGTTAGGGTTAGGGTTA (SEQ ID NO: 95) and GTTAGGGTTAGGGTTAGGGTTAG (SEQ ID NO: 96). The oligonucleotide with 24 bases is selected from the group consisting of TTAGGGTTAGGGTTAGGGTTAGGG (SEQ ID NO: 97), TAGGGTTAGGGTTAGGGTTAGGGT (SEQ ID NO: 98), AGGGTTAGGGTTAGGGTTAGGGTT (SEQ ID NO: 99), GGGTTAGGGTTAGGGTTAGGGTTA (SEQ ID NO: 100), GGTTAGGGTTAGGGTTAGGGTTAG (SEQ ID NO: 101) and GTTAGGGTTAGGGTTAGGGTTAGG (SEQ ID NO: 102). The oligonucleotide with 25 bases is selected from the group consisting of TTAGGGTTAGGGTTAGGGTTAGGGT (SEQ ID NO: 103), TAGGGTTAGGGTTAGGGTTAGGGTT (SEQ ID NO: 104), AGGMAGGGTTAGGGTTAGGGTTA (SEQ ID NO: 105), GGGTTAGGGTTAGGGTTAGGGTTAG (SEQ ID NO: 106), GGTTAGGGTTAGGGTTAGGGTTAGG (SEQ ID NO: 107) and GTTAGGGTTAGGGTTAGGGTTAGGG (SEQ ID NO: 108). The oligonucleotide with 26 bases is selected from the group consisting of TTAGGGTTAGGGTTAGGGTTAGGGTT (SEQ ID NO: 109), TAGGGTTAGGGTTAGGGTTAGGGTTA (SEQ ID NO: 110), AGGGTTAGGGTTAGGGTTAGGGTTAG (SEQ ID NO: 111), GGGTTAGGGTTAGGGTTAGGGTTAGG (SEQ ID NO: 112), GGTTAGGGTTAGGGTTAGGGTTAGGG (SEQ ID NO: 113) and GTTAGGGTTAGGGTTAGGGTTAGGGT (SEQ ID NO: 114). The oligonucleotide with 27 bases is selected from the group consisting of TTAGGGTTAGGGTTAGGGTTAGGGTTA (SEQ ID NO: 115), TAGGGTTAGGGTTAGGGTTAGGGTTAG (SEQ ID NO: 116), AGGGTTAGGGTTAGGGTTAGGGTTAGG (SEQ ID NO: 117), GGGTTAGGGTTAGGGTTAGGGTTAGGG (SEQ ID NO: 118), GGTTAGGGTTAGGGTTAGGGTTAGGGT (SEQ ID NO: 119) and GTTAGGGTTAGGGTTAGGGTTAGGGTT (SEQ ID NO: 120). The oligonucleotide with 28 bases is selected from the group consisting of TTAGGGTTAGGGTTAGGGTTAGGGTTAG (SEQ ID NO: 121), TAGGGTTAGGGTTAGGGTTAGGGTTAGG (SEQ ID NO: 122), AGGGTTAGGGTTAGGGTTAGGGTTAGGGT (SEQ ID NO: 123), GGGTTAGGGTTAGGGTTAGGGTTAGGGT (SEQ ID NO: 124), GGTTAGGGTTAGGGTTAGGGTTAGGGTT (SEQ ID NO: 125) and GTTAGGGTTAGGGTTAGGGTTAGGGTTA (SEQ ID NO: 126). The oligonucleotide with 29 bases is selected from the group consisting of TTAGGGTTAGGGTTAGGGTTAGGGTTAGG (SEQ ID NO: 127, TAGGGTTAGGGTTAGGGTTAGGGTTAGGG (SEQ ID NO: 128), AGGGTTAGGGTTAGGGTTAGGGTTAGGGT (SEQ ID NO: 129), GGGTTAGGGTTAGGGTTAGGGTTAGGGTT (SEQ ID NO: 130), GGTTAGGGTTAGGGTTAGGGTTAGGGTTA (SEQ ID NO: 131) and GTTAGGGTTAGGGTTAGGGTTAGGGTTAG (SEQ ID NO: 132). The oligonucleotide with 30 bases is selected from the group consisting of TTAGGGTTAGGGTTAGGGTTAGGGTTAGGG (SEQ ID NO: 133), TAGGGTTAGGGTTAGGGTTAGGGTTAGGGT (SEQ ID NO: 134), AGGGTTAGGGTTAGGGTTAGGGTTAGGGTT (SEQ ID NO: 135), GGGTTAGGGTTAGGGTTAGGGTTAGGGTTA (SEQ ID NO: 136), GGTTAGGGTTAGGGTTAGGGTTAGGGTTAG (SEQ ID NO: 137) and GTTAGGGTTAGGGTTAGGGTTAGGGTTAGG (SEQ ID NO: 138).

Further, the oligonucleotide sequence may comprise of a varying number of GT, GGT or GGTT, or repeats thereof.

The oligonucleotide sequence having a portion of a mammalian telomere sequence is 100% homologous to a mammalian telomere sequence comprising direct repeats of a hexanucleotide sequence (TTAGGG). In a further embodiment, the oligonucleotide sequence having a variant of a mammalian telomere sequence is less than 100% homologous to a mammalian telomere sequence comprising direct repeats of a hexanucleotide sequence (TTAGGG). In yet a further embodiment, the oligonucleotide sequence having a variant of a mammalian telomere sequence is between 40% to 88% homologous to a mammalian telomere sequence comprising direct repeats of a hexanucleotide sequence (TTAGGG). In a further embodiment, the oligonucleotide sequence having a variant of a mammalian telomere sequence is selected from the group consisting of GAGTATGAG, GTTAGGTTTAAGGTT (SEQ ID NO:6), GGTAGGTGTAGGGTG (SEQ ID NO:7), GGTAGGTGTAGGATT (SEQ ID NO: 8), GATAAGGGATTGGGAT (SEQ ID NO: 9), GGTAGGTGTAGGATTT (SEQ ID NO: 10), GGTTAGGTGTAGGTTT (SEQ ID NO: 11), GGTTAGGTGGAGGTTT (SEQ ID NO: 12), GGTTAGGTTTAGGTTT (SEQ ID NO: 13), GGTTAGGTTAAGGTTA (SEQ ID NO: 14), GGTAGGTGTAGGGTG (SEQ ID NO: 7), GGTTGGTTGGTTGGTT (SEQ ID NO: 15) and GGTTGGTTGGTTGGTTGGTT (SEQ ID NO:2).

In yet another embodiment, the oligonucleotide sequence having a portion of a mammalian telomere sequence that is 100% homologous to a mammalian telomere sequence comprising direct repeats of a hexanucleotide sequence (TTAGGG) is any oligonucleotide obtained from the mammalian telomere sequence $(TTAGGG)_n$, where n indicates the number of times (TT AGGG) are directly repeated and is more than 500.

In yet another embodiment, the oligonucleotide sequence having a portion of a mammalian telomere sequence that is 100% homologous to a mammalian telomere sequence comprising direct repeats of a hexanucloetide sequence (TTAGGG) is selected from the group consisting of GTTAGGGTT, TTAGGGTTA, GGGTTAGGG, GTTAGGGTTAG (SEQ ID NO:1), GTTAGGGTAGGGTT (SEQ ID NO:5), and GTTAGGGTTAGGGTTA (SEQ ID NO:4).

Further, the invention provides an embodiment wherein the portion of the mammalian telomere at the 3' end is a 3' overhang sequence having any of the sequence TAGGGT, AGGGTT, GGGTTA, GGTTAG, and GTTAGG, or repeats thereof. In one embodiment, the oligonucleotide with a 3' overhang sequence of a mammalian telomere, a portion thereof or variant thereof comprises TTAGGG. In a further embodiment, the oligonucleotide with a 3' overhang sequence of a mammalian telomere, a portion thereof or variant thereof is a fragment of $(TTAGGG)_n$, wherein n is 18 or more. In one embodiment, 3' overhang sequence of a mammalian telomere consists of 6 or more repeats of (TTAGGG). In another embodiment, 3' overhang sequence of a mammalian telomere is $(TTAGGG)_6$. In another embodiment, 3' overhang sequence of a mammalian telomere is $(TTAGGG)_n$, where n is between 6 and 45. In another embodiment, 3' overhang sequence of a mammalian telomere is $(TTAGGG)_n$, where n is more than 45. In another embodiment, 3' overhang sequence of a mammalian telomere is $(TTAGGG)_n$, where n is more than 65. Natural variation in the length of 3' overhang sequence of a mammalian telomere, $(TTAGGG)_n$, is reported in Cimino-Reale, Gl. et al., 2001 (Cimino-Reale, Gl. et al., (2001) The length of telomeric G-rich strand 3-overhang measured by oligonucleotide ligation assay. Nucleic Acids Res 29(7): e35). In yet a further embodiment, the fragment of $(TTAGGG)_n$ is selected from the group consisting of TT, GTTAGGGTT, TTAGGGTTA, GGGTTAGGG, GTTAGGGTTAG (SEQ ID NO:1), GTTAGGGTTAGGGTT (SEQ ID NO:5) and GTTAGGGTTAGGGTTA (SEQ ID NO:4). In yet another embodiment, the variant has between 40% to 99% homology to a reference sequence, (TTAGGG)$_n$, comprising direct repeats of a hexanucleotide sequence of a mammalian telomeric 3' overhang sequence, TTAGGG. In yet another embodiment, the oligonucleotide is free of cytosine base. The variant is selected from the group consisting of GAGTATGAG, GTTAGGTTTAAGGTT (SEQ ID NO:6), GGTAGGTGTAGGGTG (SEQ ID NO:7), GGTAGGTGTAGGATT (SEQ ID NO:8), GATAAGGGATTGGGAT (SEQ ID NO:9), GGTAGGTGTAGGATTT (SEQ ID NO:10), GGTTAGGTGTAGGTTT (SEQ ID NO:11), GGTTAGGTGGAGGTTT (SEQ ID NO:12), GGTTAGGTTTAGGTTT (SEQ ID NO:13), GGTTAGGTTAAGGTTA (SEQ ID NO:14), GGTAGGTGTAGGGTG (SEQ ID NO:7), GGTTGGTTGGTTGGTT (SEQ ID NO:15) and GGTTGGTTGGTTGGTTGGTT (SEQ ID NO:2). In one embodiment, the variant comprises less than 10% cytosines. In yet another embodiment, the variant is free of cytosine base.

Suitable oligonucleotide sequences may be at least about 70% identical, preferably at least about 80% identical, more preferably at least about 90% identical and most preferably at least about 95% identical (e.g., 95%, 96%, 97%, 98%, 99%, 100%) to the reference oligonucleotide sequences of the present invention (i.e., see examples herein) when the comparison is performed by a BLAST algorithm wherein the parameters of the algorithm are selected to give the largest match between the respective sequences over the entire length of the respective reference sequences.

In accordance with the practice of the invention, the oligonucleotide may be a modified oligonucleotide. For example, the modified oligonucleotide may comprise a modified phosphodiester backbone, modified nucleoside, modified base, modified sugar or a combination thereof. Modified phosphodiester backbones may include any of a phosphorothioate, methylphosphonate, inverted 5'-5' linkage, inverted 3'-3' linkage, biotin-modified on the 5' end, biotin-modified on the 3' end, or N-(2-aminoethyl)-glycine repeat units linked by peptide bonds. Modified nucleosides may include any of 2'-fluoro adenosine, 2'-fluoro deoxyguanosine, 2'-fluoro deoxyuridine, 2'-O methyl adenosine, 2'-O methyl guanosine, 2'-O methyl uridine, 5-bromouridine, propyne deoxyuridine, or biotin-modified nucleoside. Modified bases may include any of a thymine dimer, biotin-modified thymine, and biotin-modified base. Suitable examples of modified sugars include, but are not limited to, L-ribose, D-ribose, L-deoxyribose, dideoxyribose, and biotin-modified sugar.

The oligonucleotide sequence of the composition may be a sequence which is guanine-rich and forms a quadruplex secondary structure. For example, the quadruplex secondary structure may be formed within a single oligonucleotide or between two or more oligonucleotides. In another example, the quadruplex structure comprises one oligonucleotide chain, two oligonucleotide chains or four oligonucleotide chains. In yet another example, the quadruplex secondary structure may facilitate uptake of the oligonucleotide sequence into a cell, be resistant to degradation by nucleases, and/or permit accumulation of the oligonucleotide in the nucleus. In one embodiment, the quadruplex structure comprises Hoogsteen hydrogen bonds between guanines. In a further embodiment, the quadruplex structure comprises two or more square planar structure(s) or guanine tetrad(s). In yet another embodiment, each square planar structure or guanine tetrad is formed by four guanines forming Hoogsteen hydrogen bonds. In yet another embodiment, two or more square planar structures or guanine tetrads can stack on top of each other to form a quadruplex structure.

The oligonucleotide sequence of the composition may be a sequence which is guanine-rich and forms a quadruplex secondary structure. In one embodiment, the quadruplex structure is free of Watson-Crick basepair. In yet another embodiment, the quadruplex structure comprises non-Wason-Crick basepairs.

Merely by way of example, in one embodiment, the oligonucleotide sequence comprises at least 30% guanine (G) content. In a further embodiment, the oligonucleotide sequence comprises less than 70% guanine (G) content. In yet a further embodiment, the oligonucleotide sequence comprises between 30% and 70% guanine (G) content (e.g., 33%, 38%, 40%, 44%, 45%, 47%, 50%, 60%, 67%).

In another example, in one embodiment, the oligonucleotide sequence is free of cytosine (C) content. In a further embodiment, the oligonucleotide sequence comprises less than or equal to 10% cytosine (C) content. In yet a further embodiment, the oligonucleotide sequence comprising less than or equal to 10% cytosine content is CCTTGGTTGGTTGGTTGGTT (SEQ ID NO:3).

In yet another example, in one embodiment, the oligonucleotide sequence comprises between 30% and 70% guanine (G) content and is free of cytosine (C) content. In a further embodiment, the oligonucleotide sequence additionally comprises adenine content or thymine content. In yet a further embodiment, the oligonucleotide sequence additionally comprises adenine content and thymine content.

In an embodiment, a composition of the invention comprises an oligonucleotide for treating, inhibiting and/or preventing auditory impairment, a second active agent for treating, inhibiting and/or preventing auditory impairment and a carrier. In an embodiment, the oligonucleotide has sequence comprising a portion of a mammalian telomere sequence or a variant of a mammalian telomere sequence. In another embodiment, the oligonucleotide has sequence consisting of a portion of a mammalian telomere sequence or a variant of a mammalian telomere sequence. In an embodiment, the mammalian telomere sequence is a direct repeat of a hexanucleotide TTAGGG, which may be described as (TTAGGG)n, wherein "n" is the number of TTAGGG repeats. In one embodiment, the oligonucleotide has the length of any of the oligonucleotide of the invention. In a further embodiment, the oligonucleotide has the sequence of any of the oligonucleotide of the invention. In an embodiment, the oligonucleotide of the invention forms a quadruplex structure. In an embodiment, the second active agent is any of the active agent of the invention.

Suitable carriers for pharmaceutical compositions include any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Such compositions may also be formulated within various lipid compositions, such as, for example, liposomes as well as in various polymeric compositions, such as polymer microspheres.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The kit can contain a pharmaceutical composition that includes one or more agents of the invention effective for treating, inhibiting and/or preventing an auditory impairment and an acceptable carrier or adjuvant, e.g., pharmaceutically acceptable buffer, such as phosphate-buffered saline, Ringer's solution or dextrose solution. The kit may include a second active agent. The second active agent may be useful for treating, inhibiting and/or preventing auditory impairment. Further, the second active agent may promote survival of cochlear outer hair cells. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for an auditory impairment.

The label and/or the instructions can indicate directions for in vivo use of the pharmaceutical composition. The label and/or the instructions can indicate that the pharmaceutical composition is used alone, or in combination with another agent to treat an auditory impairment.

The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

The following example is intended merely to illustrate the practice of the present invention and is not provided by way of limitation. The disclosures of all patent and scientific literatures cited herein are expressly incorporated in their entirety by reference.

Example 1

There were three experimental objectives. The first, was to determine whether or not t-oligo treatment could recover outer hair cell function when administered after exposure to a damaging level of noise. If hair cell functions could be recovered then it might also be possible to recover retrochlear (e.g., neural) functions. Distortion product otoacoustic emissions were used to evaluate outer hair cell functions and auditory brainstem responses were used to measure retrocochlear functions. The second, was to determine whether t-oligo treatment induced any change in gene or protein expression of DNA repair factors. The genes or proteins involved were ATM, p53, XPC, XPF, XPG, and ATM/ATR/DNA-PKs substrates. The third, was to determine whether t-oligo induced a dose-response effect in the cochlea and whether there was also a temporal effect on gene expression within the cochlea.

Materials and Methods

Animals:

Six male Long-Evans rats (100 g at 1 months old) were acquired from Harlan Laboratories, Inc. (Livermore, Calif. USA) and served as subjects in these experiments. The animals were housed at the Veterinary Medical Unit (VMU) at the Loma Linda Veteran's Affairs Hospital (Loma Linda, Calif. USA). All experimental protocols were approved by the Institutional Animal Care and Use Committee at the Loma Linda Veteran's Affairs Hospital. When the animals arrived at the VMU they were given one week to acclimate to their new environment. Distortion Product Otoacoustic Emissions (DPOAE): The animals were anaesthetized with ketamine/xylazine (75/5 mg/kg, i.m.), then placed ventrally on a 7"×15" surgical table with built-in temperature control to maintain normal body temperature (37°±1° C.). All measurements were obtained in a double-walled sound-isolation chamber (Industrial Acoustics Company Inc., Bronx, N.Y. USA). A probe assembly was physically and acoustically coupled to the external auditory meatus via an ER3-34 infant silicon tip (Etymotic Research, Elk Grove Village, Ill. USA). The probe assembly consists of two polyethylene tubes coupled to two separate realistic dual radial horn tweeters (Radio Shack, Tandy Corp., Ft Worth, Tex. USA). These tweeters were used to present two stimulus pure tones: $f_1$ and $f_2$. These pure tones were acoustically mixed in the external auditory meatus to avoid artifactual distortion. The probe assembly also consisted of a pre-amplifier microphone cable coupled to an ER-10B+ emission microphone (Etymotic Research). This allowed for the detection and amplification of acoustic emissions and the recording of background noise in the external auditory meatus. All elements of the probe assembly were controlled through a customized signal presentation, acquisition and analysis algorithm written in LabVIEW version 7.1 (National Instruments, Austin, Tex., USA). This LabVIEW algorithm was also used to drive a PCI-4461 computer-based digital signal processing board (National Instruments).

Auditory Brainstem Response (ABR):

The ABR recordings were obtained after the animals were given general anesthesia (ketamine/xylazine, 75/5 mg/kg, i.m.). Each animal was ventrally positioned on a 7"×15" surgical table with built-in temperature control. Core body temperature was monitored with a rectal probe attached to a 43TD telethermometer (Yellow Springs Instrument Company, Inc., OH., USA) and maintained at 37°±1° C. All recordings were obtained while the animals were staged inside a double-walled sound-isolation chamber (Industrial Acoustics Company Inc., Bronx, N.Y. USA). A five electrode montage was used to conduct 2-channel differential recordings. Two noninverting electroencephalographic needle (0.4 mm; Pt/Ir) electrodes (VIASYS NeuroCare, Madison, Wis., USA) were placed on the vertex, another two below the right and left mastoids (inverting) and one electrode (common) was placed in the dorsum close to the tail.

Noise Exposure:

The noise was a 5.6 to 11.5 kHz band at 105 dB SPL for 16 hours. This noise dose was chosen because in rats, this dose results in permanent sensorineural loss. The animals were unrestrained in individual cages within a reverberant 40 liter chamber. Vifa D25AG-05 speakers (Vifa International A/S, Videbaek, Denmark) were suspended approximately 5 cm above the cages. A HCA1000A Parasound Amplifier (Parasound Products, Inc., San Francisco, Calif. USA) was used to drive the speakers while a Frequency Device 9002-Dual-Channel Filter/Amplifier Instrument (Frequency Device Inc., Haverhill, Mass. USA) provided band-pass filtering to the output from a DS335 Function-Generator (Stanford Research System, Menlo Park, Calif. USA). Calibration of the noise to target SPLs was conducted at the beginning of exposure and at each hour thereafter.

Transtympanic Injections (TTI):

Injections were conducted while the animals were anesthetized. Under an operating microscope, a single use 22G 1¼ sterile needle (Becton Dickson, USA) with 1 ml syringe were used to make a single incision in pars tensa of the tympanic membrane. T-oligo dissolved in saline or saline by itself was injected through the incision at a volume of 50 µl. The animal was then left undisturbed for 30 minutes with the treated ear facing upwards. This protocol was then repeated for the opposite ear. The animals received TTI of saline or T-oligo (5'-GTTAGGGTTAGGGTTA-3') (SEQ ID NO: 4) immediately after the 16 hour noise exposure.

RNA and Protein Extraction:

Total RNA and protein were simultaneously isolated from the cochlea by using the RNA/Protein Purification Kit (Norgen BioTEK corp., Canada). Frozen tissues (80-100 mg) were ground thoroughly in a mortar using a pestle and then homogenized in 1.2 ml of lysis solution. The lysates were then transferred into an RNase-free microcentrifuge tube and Spin for 2 min at 14,000 g. The supernatant were transferred to a new microcentrifuge tube and then loaded onto a gDNA removal column and centrifuge for 1 min at 14,000 g. The flow-through was then loaded onto an RNA/Protein purification column for RNA and protein purification. The bound RNA and proteins were then released in 50 µl and 100 µl elution buffer from the binding column respectively. All steps adhered to the instructions provided by the manufacturer (Norgen BioTEK corp., Canada). RNA concentrations were determined by using Nanodrop 2000 (Thermo Scientific, USA). Protein concentrations were determined by using Pierce BCA Protein Assay kit (Thermo Scientific, USA) and Synergy 2 Multi-Mode Microplate Reader (BioTek, USA). Purified total RNA and proteins were stored at −80° C. till use. The purified RNA samples were converted to cDNA and then subjected to quantitative PCR. The purified protein samples were then subjected to Western blots.

Statistical Analyses:

Analysis of variance (ANOVA) and post-hoc computations were used to determine statistical significant differences. P-values<0.05 were considered significant.

Results

Recovery of Outer Hair Cell Function (FIGS. 1 & 2):

FIG. 1 shows recovery of cochlear outer hair cell function with t-oligo treatment in a single subject research design. At baseline both left (left panel) and right (right panel) ear outer hair cell function was measured with the 2f1–f2 distortion product otoacoustic emissions. The y-axis illustrates the level of the outer hair cell responses while the x-axis illustrates the frequency location of the cells along the basilar membrane. Note the robust response (black circles) from both ears, also note that these responses are significantly elevated above the biological and instrumental noise floor (solid gray line). The animal was then exposed to a damaging noise dose (105 dB SPL for 16 hours). The vertical gray bar represents the bandwidth of the damaging noise (5.6 to 11.5 kHz). Within 24 hours after the noise exposure, the left ear received saline (vehicle control) via transtympanic injection while the right ear received t-oligo via transtympanic injection. At 1 week after this noise dose, both the right and left ears showed poor outer hair cell function. Note that the outer hair cell responses (black stars) were depleted into the noise floor. At two months after the noise exposure the left ear which received saline continues to show outer hair cell responses (open triangles) that were embedded in the noise floor. However, the right ear which received t-oligo exhibited outer hair cell responses that were significantly elevated above the noise floor.

FIG. 2 assesses recovery of outer hair cell function with t-oligo treatment in an experimental research design with 6 animals. Panels 2A and 2B are outer hair cell responses measured with the $2f_1-f_2$ distortion product otoacoustic emissions while Panels 2C and 2D are outer hair cell responses measured with the $2f_2-f_1$ distortion product otoacoustic emissions. At baseline both left (panels 2A and 2C) and right (panels 2B and 2 D) ear outer hair cell function was measured. The y-axis illustrates the level of the outer hair cell responses while the x-axis illustrates the frequency location of the cells along the basilar membrane. Note the robust response (black circles) from both ears, also note that these responses are significantly elevated above the biological and instrumental noise floor (solid gray line). The animals were then exposed to a damaging noise dose (105 dB SPL for 16 hours). The vertical gray bar represents the bandwidth of the damaging noise (5.6 to 11.5 kHz). Within 24 hours after the noise exposure, the left ears received saline (vehicle control) via transtympanic injection while the right ears received t-oligo via transtympanic injection. At 1 week after this noise dose, both the right and left ears showed poor outer hair cell function (black stars). Note that this poor function can be seen in both the $2f_1-f_2$ and the $2f_2-f_1$ measurements as suppressed responses relative to the original responses at baseline. At two months after the noise exposure the left ear which received saline continues to show outer hair cell responses (open triangles) that were suppressed relative to that at baseline. However, the right ear which received t-oligo exhibited $2f_1-f_2$ levels that were significantly elevated above the noise floor. Also note that the $2f_2-f_1$ levels showed almost complete recovery of function. Each data point in all panels represent the mean data from 6 animals and the error bars are standard errors (±).

In summary, cochlear hair cell function was measure with the 2f1–f2 and the 2f2–f1 distortion product otoacoustic emissions (DPOAEs) before (baseline) and after noise trauma. In the ears that received t-oligo, DPOAEs were present at high/robust levels at baseline and at 2 months after the injury. However, in the opposite ears that served as vehicle-control, DPOAE levels were present at high/robust levels at baseline but were severely depressed at 2 months after the injury. At 1 week after the noise exposure both ears (right and left) showed depressed DPOAE levels. This indicates that both ears were traumatized by the noise exposure. However, only the ears that were treated with t-oligo showed improvement while the opposite ear (not treated with t-oligo) showed no significant improvement. Given that t-oligo was administered with 24 hours after the noise injury, these data indicate that t-oligo is effective as a treatment for noise induced outer hair cell dysfunction.

Protection from Noise Induced Retrocochlear Dysfunctions (FIG. 3):

Cochlear hair cells are sensory cells that detect information (e.g., sound) then facilitate the transduction and transmission of the information to neurons so that the brain can process the original information. This retrocochlear capacity was measured before and after the noise injury with wavelet analyses from the auditory brainstem response.

Figures 3A, 3B, 3C:
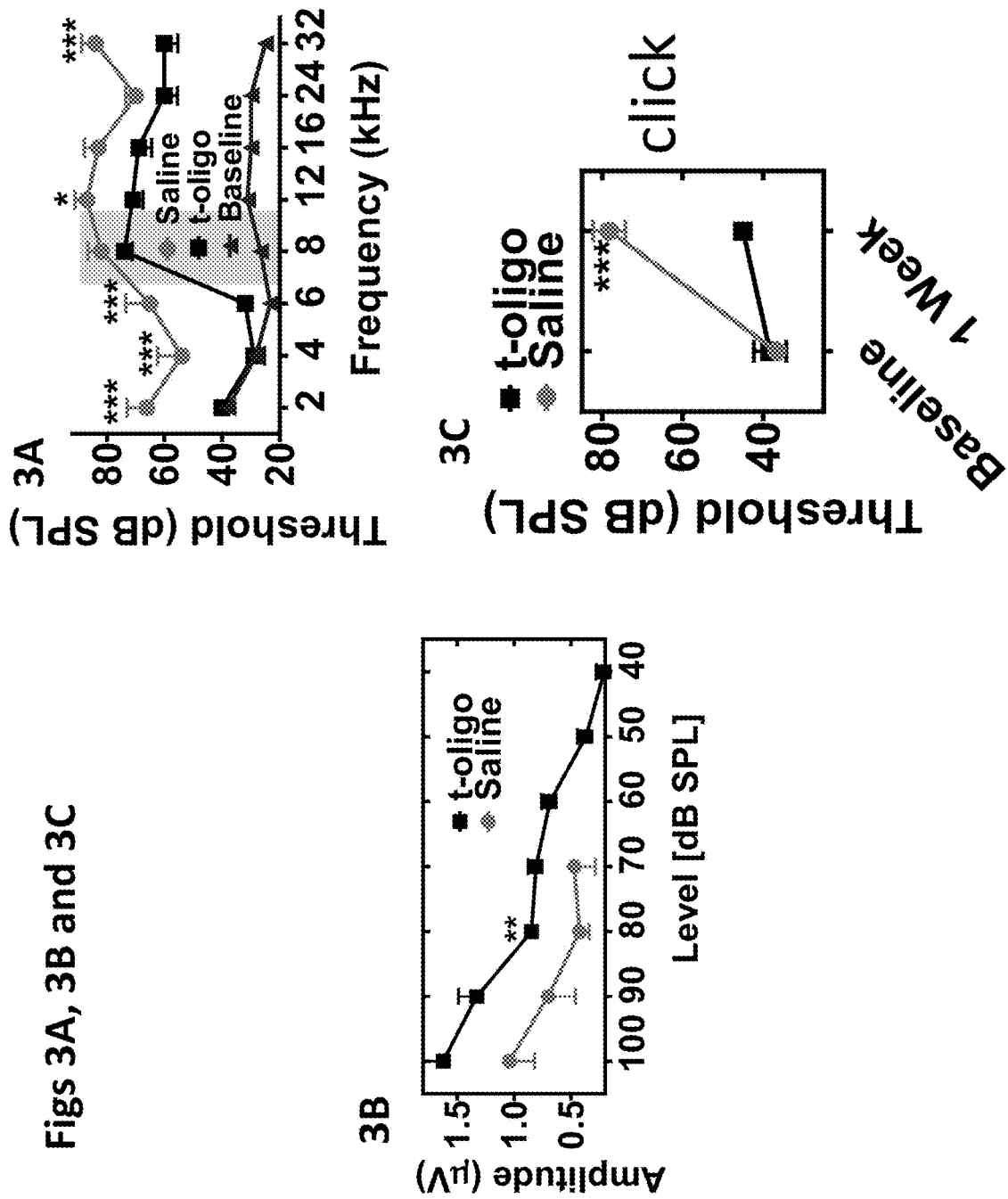
FIG. 3A-3C. T-oligo treatment limits the magnitude of retrocochlear dysfunctions at 1 week and 2 months after exposure to a damaging level of noise. Panel A shows frequency specific threshold shifts for the auditory brainstem response at baseline (triangles) prior to noise exposure and saline-vehicle (circles) and t-oligo (squares) treatment after noise exposure, Panel B shows voltage response from auditory neurons generated from the auditory brainstem after t-oligo treatment (squares) or saline-vehicle treatment (circles) at 2 months after exposure to a damaging level of noise. Panel C shows click threshold shifts for the auditory brainstem response at baseline prior to noise exposure for the ears to be treated with saline or t-oligo and saline or t-oligo treated ears 1 week after exposure to damaging noise. Each data point in all panels represent the mean data from 6 animals and the error bars are standard errors (±). Statistically significant differences between the saline and t-oligo treatment conditions are indicated with asterisk, such that $*=p<0.05$, $=p<0.01$ and $*=p<0.001$.

FIG. 3 shows that t-oligo treatment limits the magnitude of retrocochlear dysfunctions at 1 week and 2 months after exposure to a damaging level of noise. Panel A shows frequency specific threshold shifts for the auditory brainstem response. Note that saline-vehicle treatment (circles) after the noise exposure resulted in significantly worse (higher) thresholds relative to thresholds at baseline (triangles). T-oligo treatment (squares) also resulted in significantly worse (higher) thresholds relative to thresholds at baseline. However, thresholds after t-oligo treatment was better (lower) than that of saline treatment and these differences were statistically significant ($p<0.001$). These results indicate that the sensitivity of the auditory system rostral to the cochlea, is better preserved with t-oligo treatment relative to saline vehicle-treatment. Panel B reveals that the voltage response from auditory neurons generated from the auditory brainstem is more prominent after t-oligo treatment relative to saline-vehicle treatment at 2 months after exposure to a damaging level of noise. Furthermore, voltage responses could be recorded with stimulus intensities as low as 40 dB after t-oligo treatment while a loud intensity of up to 70 dB was needed to record voltage responses after saline treatment. Panel C shows click threshold shifts for the auditory brainstem response. At baseline auditory function for both the saline and t-oligo treatment conditions were similar but 1 week after the noise exposure the saline treated ears resulted in significant hearing loss while the t-oligo treated ears resulted in a slight loss. Each data point in all panels represent the mean data from 6 animals and the error bars are standard errors (±). Statistically significant differences between the saline and t-oligo treatment conditions are indicated with asterisk, such that $*=p<0.05$, $=p<0.01$ and $*=p<0.001$.

In summary, before the noise exposure (baseline), retrocochlear sensitivity (W1 threshold) was low (good) but after the noise injury thresholds were severely elevated (bad). In the ears that received t-oligo, retrocochlear sensitivity was better ($p<0.05$) than that of the opposite ears that were not treated with t-oligo. An indication that t-oligo induced recovery of hair cell function (FIGS. 1 & 2) resulted in preservation of retrocochlear functions (FIG. 3). This was confirmed with voltage recordings from cochlear neurons, where the measured voltage from ears treated with t-oligo was significantly more robust than that measured from ears that were not treated with t-oligo (FIG. 3).

T-Oligo Induced Activation of a Protective p53/XPC Response (FIGS. 4, 5 & 6):

Transtympanic administration of t-oligo resulted in an increase in phosphorylation of the p53 protein at serine 15 (p53ser15). As shown in FIG. 4, t-oligo activates p53 in the mammalian cochlea. Immunoblotting assays reveal that under normal conditions p53 is expressed in the cochlea with low activation (phosphorylation). After noise exposure there is significant activation with modest increase in total p53. T-oligo treatment increases the activation of p53 but lowers the total amount of p53 (probably to prevent apoptosis). T-oligo+noise elicits similar results, wherein there is increased activation of p53 occurred with a decrease in total p53.

The increased activation of p53 is accompanied by an increase in global DNA damage signaling. As shown in FIG. 5, both t-oligo and noise exposure elicits global DNA damage signaling in the mammalian cochlea. Under normal (control) conditions there is little or no DNA damage signaling in the cochlea. Global DNA damage signaling was determined via Western blot detection of protein substrates with ATM/ATR/DNA-Pkc target consensus motifs (hydrophobic aa-Ser*/Thr*-hydrophilic aa) such as Leu(Ser*/Thr*)Gln (* indicates phosphorylated site). After noise, t-oligo and t-oligo+noise treatment there was an increase in global DNA damage signaling.

FIG. 6 shows a model for how t-oligo treatment increases the expression of protective DNA repair genes in the mammalian cochlea. Panel A shows a hypothetical model to explain the protective effect of t-oligo treatment. T-oligo activates DNA damage signaling through the ATM/ATR/DNA-Pkc kinase family which leads to phosphorylation of p53. P53 then transcriptionally activates DNA repair genes such as XPC. XPC then initiates DNA repair processes such as NER. Alternatively, t-oligo may activate p53 in a manner that is independent of the ATM/ATR/DNA-Pkc family and p53 may then activate NER and other types of DNA repair processes. Panel B shows that t-oligo+noise may increase ATM gene expression, although this increase was modest, however, both p53 and XPC gene expression was significantly elevated. Statistically significant differences between the experimental conditions are indicated with asterisk, such that $*=p<0.05$, and $**=p<0.01$. Interestingly, combined t-oligo and noise exposure caused a 15-fold increase in the expression of the p53 gene (FIG. 6B, p53 gene (fold Δ)) and a 4-fold increase in the xeroderma pigmentosum-C (XPC) gene (FIG. 6B, XPC gene (fold Δ)). XPC is a pro-cell survival gene that has a p53 response element in its promotor region, therefore it is transcriptionally regulated by p53.

In summary, these combined results suggest that t-oligo actives a p53/XPC pro-survival response in the mammalian cochlea.

Figure 7:
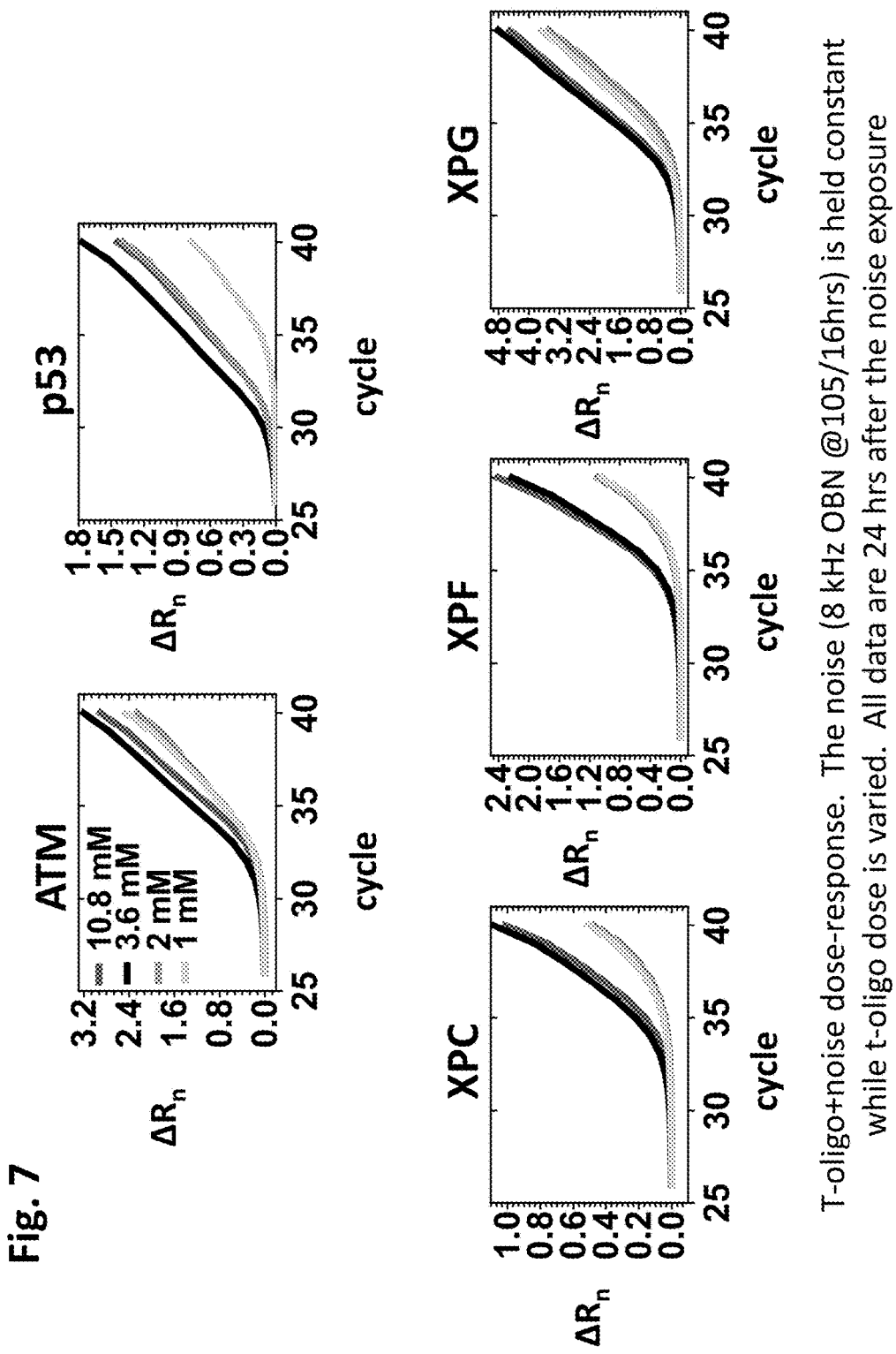
FIG. 7. Dose-response effects on expression of DNA repair genes, ATM, p53, XPC, XPF and XPG, within the mammalian cochlea at 24-hrs after exposure to damaging noise (8 kHz OBN @ 105/16 hrs) and subsequent treatment with different concentrations of t-oligo (1 mM, 2 mM, 3.6 mM, or 10.8 mM t-oligo), as determined by quantitative real-time PCR.
Figure 8:
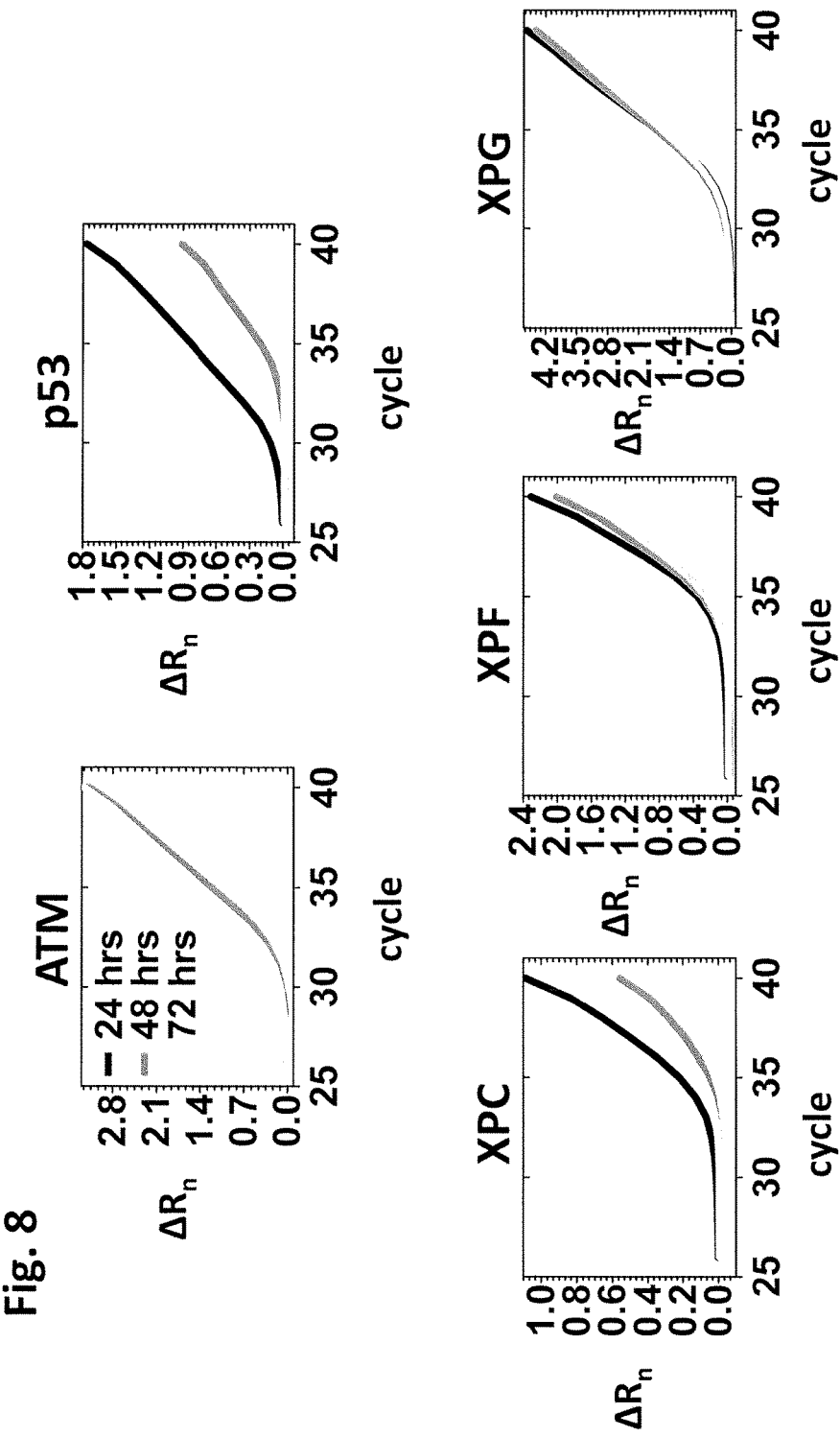
FIG. 8. Time course of t-oligo treatment on gene expression of DNA repair genes, ATM, p53, XPC, XPF and XPG, within the mammalian cochlea at 24-hrs, 48 hrs and 72 hrs after exposure to damaging noise (8 kHz OBN @ 105/16 hrs) and subsequent treatment with 18 mg/ml t-oligo, as determined by quantitative real-time PCR. Note ATM, XPF and XPG genes showed little or no changes over time, however, the p53 and XPC genes decrease with time.

T-Oligo Increases the Expression of Protective DNA Repair Genes (FIGS. 7 & 8).

The expression of ATM and various nucleotide excision repair genes were quantifies after t-oligo+noise treatments. The results suggest that increasing t-oligo's concentration resulted in an increase in gene expression. FIG. 7 shows dose-response effects within the mammalian cochlea from t-oligo treatment. After exposure to noise, t-oligo was administered at 4 different concentrations then 24 hours later the expression of individual genes was quantified in real-time. The y-axis of each plot shows gene expression level while the x-axis of each plot shows the time course of the reaction in cycles. Note that for each DNA repair gene (ATM, p53, XPC, XPF & XPG), there is an increase in gene expression level with an increase in the concentration of t-oligo. Furthermore, the increase in gene expression was stable out to 3 days, as shown in FIG. 8.

FIG. 8 shows time course effects of t-oligo within the mammalian cochlea. After exposure to noise, t-oligo was administered and then the cochlea was harvested at 3 time points (24, 48 & 72 hours) following the t-oligo treatment. The expression of individual genes was quantified in real-time. The y-axis of each plot shows gene expression level while the x-axis of each plot shows the time course of the reaction in cycles. The ATM, XPF and XPG genes showed little or no changes over time, however, the p53 and XPC genes decrease with time. This suggest that t-oligo could provide protection from hearing loss by increasing the expression of protective DNA repair genes and this protection may persist for days after the noise exposure.

Discussion

Noise induced hearing loss (NIHL) is one of the most frequent occupational injuries (Nelson et al., 2005). In addition to hearing loss and tinnitus (ringing in the ear), noise over-exposure can lead to auditory dysfunctions even in the presence of normal thresholds (Lindblad et al., 2014). At least two type of permanent noise injury can result from noise over-exposure. One is noise trauma which results in rapid rupture or tearing of cochlear structures, while the other, more common, type is metabolic stress. Metabolic stress results in changes within hair cells that ultimately lead to cellular dysfunctions and/or cell death. Unlike noise trauma, metabolic changes are more amenable to therapeutic interventions. Currently, there is no widely accepted biomedical treatment for NIHL and there are several reasons why (reviewed in Oishi & Schacht, 2011). One important reason is that metabolic noise stress triggers a large variety of independent and complementary pathophysiologic cascades. In order to preserve auditory function, hearing researchers have experimentally blocked or targeted several cascades with antioxidants, calcium inhibitors, energy enhancers, growth factors, caspase inhibitors and an impressive variety of other bioactive compounds (Oishi & Schacht, 2011; Ohlemiller, 2008; Le Prell et al., 2007). These efforts have provided important information about NIHL and the mechanisms involved. However, there is still no established clinical therapy beyond the fitting of hearing aids after permanent loss has already developed.

The cell death cascades that are induced by noise exposure have at least one thing in common; they all ultimately result in DNA damage, whether directly (e.g., ROS) or indirectly (e.g., elevated calcium levels). Indeed, our research has shown that noise exposure damages the DNA in auditory sensory hair cells within 24 hrs after the exposure (Guthrie & Xu, 2011). This DNA damage is easily detected through immunohistochemical localization of γ-H2Ax, a DNA damage marker. Other research groups have also demonstrated the presence of DNA damage due to noise over-exposure (Kamio et al., 2012; Hu et al., 2006; van Campen et al., 2002). DNA damage may occur within mitochondria and the nucleus, although mitochondrial DNA (mtDNA) can be replenished through replication; nuclear DNA (nDNA) is expected to last the entire life-span of adult cells that cannot replicate (e.g. hair cells). If DNA damage is a consequence of noise over-exposure then cellular mechanisms for repairing such damage must be vital to the pathogenesis of metabolic stress. For instance, functional polymorphisms in DNA repair genes have recently been found to lower human susceptibility to NIHL (Shen et al., 2014). This is particularly important because we have provided preliminary evidence to suggest that hair cells and the majority of spiral ganglion neurons are poor at mobilizing DNA repair pathways (Guthrie & Xu, 2012; Guthrie, 2008). Poor DNA repair among cochlear hair cells may represent a significant leap forward in understanding why these cells are so vulnerable to noise over-exposure and other forms of stress such as chemical ototoxicants and even presbycusis. If DNA damage is common to most noise induced pathophysiologic cascades and cochlear hair cells are poor at DNA repair, then efforts to improve DNA repair would provide a major break-through in the medical management of hearing loss. Repairing damaged DNA after noise injury could be beneficial as a stand-alone therapy or combined with existing approaches (e.g., antioxidants, calcium inhibitors, etc.) such that both DNA damage and mechanisms up-stream (e.g., ROS and high levels of calcium) to DNA damage are targeted. Therefore, the major significance of the current work is the real possibility of improving DNA repair within cochlear hair cells, so that these cells are better able to restore gene function and preserve hearing. If successful, this will open an exciting new area of auditory cell biology and simultaneously introduce novel approaches to the medical management of hearing loss.

REFERENCES

Guthrie O W, Xu H. Noise exposure potentiates the subcellular distribution of nucleotide excision repair proteins within spiral ganglion neurons. Hear Res. 2012 December; 294(1-2):21-30. doi: 10.1016/j.heares.2012.09.001. Epub 2012 Sep. 27. PubMed PMID: 23022597.

Guthrie O W, Xu H. Reduced phosphorylation of histone variant H2Ax in the organ of Corti is associated with otoprotection from noise injury. Otolaryngology, 2013, 3, 131. doi: 10.4172/2161-119X.1000131.

Guthrie O W. Preincision complex-I from the excision nuclease reaction among cochlear spiral limbus and outer hair cells. J Mol Histol. 2008 December; 39(6):617-25. doi: 10.1007/s10735-008-9202-1. Epub 2008 Nov. 1. PubMed PMID: 18979173.

Hu B H, Henderson D, Nicotera T M. Extremely rapid induction of outer hair cell apoptosis in the chinchilla cochlea following exposure to impulse noise. Hear Res. 2006 January; 211(1-2):16-25. Epub 2005 Oct. 10. PubMed PMID: 16219436.

Kamio T, Watanabe K, Okubo K. Acoustic stimulation promotes DNA fragmentation in the Guinea pig cochlea. J Nippon Med Sch. 2012; 79(5):349-56. PubMed PMID: 23123391

Le Prell C G, Yamashita D, Minami S B, Yamasoba T, Miller J M. Mechanisms of noise-induced hearing loss indicate multiple methods of prevention. Hear Res. 2007 April; 226(1-2):22-43. Epub 2006 Dec. 4. Review. PubMed PMID: 17141991; PubMed Central PMCID: PMC1995566.

Lindblad A C, Rosenhall U, Olofsson A, Hagerman B. Tinnitus and Other Auditory Problems—Occupational Noise Exposure below Risk Limits May Cause Inner Ear Dysfunction. PLoS One. 2014 May 14; 9(5):e97377.

Nelson D I, Nelson R Y, Concha-Barrientos M, Fingerhut M. The global burden of occupational noise-induced hearing loss. Am J Ind Med. 2005 December; 48(6):446-58. PubMed PMID: 16299704.

Ohlemiller K K. Recent findings and emerging questions in cochlear noise injury. Hear Res. 2008 November; 245(1-2):5-17. doi: 10.1016/j.heares.2008.08.007. Epub 2008 Aug. 29. Review. PubMed PMID: 18790034; PubMed Central PMCID: PMC2610263.

Oishi N, Schacht J. Emerging treatments for noise-induced hearing loss. Expert Opin Emerg Drugs. 2011 June; 16(2):235-45. doi: 10.1517/14728214.2011.552427. Epub 2011 Jan. 20. Review. PubMed PMID: 21247358; PubMed Central PMCID: PMC3102156

Shen H, Cao J, Hong Z, Liu K, Shi J, Ding L, Zhang H, Du C, Li Q, Zhang Z, Zhu B. A functional Ser326Cys polymorphism in hOGG1 is associated with noise-induced hearing loss in a Chinese population. PLoS One. 2014 Mar. 5; 9(3):e89662. PubMed PMID: 24599382; PubMed Central PMCID: PMC3943766.

Van Campen L E, Murphy W J, Franks J R, Mathias P I, Toraason M A. Oxidative DNA damage is associated with intense noise exposure in the rat. Hear Res. 2002 February; 164(1-2):29-38. PubMed PMID: 11950522.

What is claimed is:

1. A method of inhibiting or treating an auditory impairment associated with outer hair cells of the cochlea in a subject comprising administering to said subject an effective amount of a composition comprising, as an active agent, an oligonucleotide sequence having a portion of a mammalian telomere sequence or a variant of a mammalian telomere sequence so as to preserve or restore outer hair cell function, preserve or restore retrocochlear function, and/or improve DNA repair, thereby inhibiting or treating the auditory impairment in the subject.

2. The method of claim 1, wherein the composition increases activation of p53 without an increase in p53 total protein concentration sufficient to induce apoptosis of cochlear outer hair cells.

3. The method of claim 1, wherein the auditory impairment is selected from a group consisting of temporary hearing loss, permanent hearing loss, sensory hearing loss, sensorineural hearing loss, tinnitus, loudness recruitment, hyperacusis, diplacusis and speech intelligibility deficits.

4. The method of claim 1, wherein the oligonucleotide sequence is isolated from a telomere.

5. The method of claim 1, wherein the oligonucleotide is a modified oligonucleotide.

6. The method of claim 1, wherein the composition is administered topically, by injection, as a swab, as a patch, as a droplet, as a stream, as an aerosol, by an implant, by a device generating a voltage potential, by a nanoparticle, by a projectile, in an aqueous solution, in saline solution, in a non-aqueous solution, in glycerol, as a solid, as a fluid, as a micelle, as a salt, as a complex with a metal, as a complex with a counter ion, as a complex with a lipid, or as a conjugate with a cell targeting agent.

7. The method of claim 1, wherein the oligonucleotide having a portion of a mammalian telomere sequence that is 100% homologous to a mammalian telomere sequence comprising direct repeats of a hexanucleotide sequence (TTAGGG) is selected from the group consisting of: GTTAGGGTT, TTAGGGTTA, GGGTTAGGG, GTTAGGGTTAG (SEQ ID NO. 1), GTTAGGGTTAGGGTT (SEQ ID NO. 5), and GTTAGGGTTAGGGTTA (SEQ ID NO. 4).

* * * * *

SEQUENCE LISTING

<160> NUMBER OF SEQ ID NOS: 138

<210> SEQ ID NO 1
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 1
gttagggtta g                                                          11

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 2
ggttggttgg ttggttggtt                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic sequence

<400> SEQUENCE: 3
ccttggttgg ttggttggtt                                                 20

<210> SEQ ID NO 4
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Portion of human telomeric sequence

<400> SEQUENCE: 4
gttagggtta gggtta                                                     16

<210> SEQ ID NO 5
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence

<400> SEQUENCE: 5
gttagggtta gggtt                                                      15

<210> SEQ ID NO 6
<211> LENGTH: 15
<212> TYPE: DNA
<213> ORGANISM: Artificial Sequence
<220> FEATURE:
<223> OTHER INFORMATION: Synthetic sequence

<400> SEQUENCE: 6

```
gttaggttta aggtt                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic sequence

<400> SEQUENCE: 7
ggtaggtgta gggtg                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic sequence

<400> SEQUENCE: 8
ggtaggtgta ggatt                                                    15

<210> SEQ ID NO 9
<211> LENGTH: 16
<212> TYPE: DNA
<213> ORGANISM: Artificial Sequence
<220> FEATURE:
<223> OTHER INFORMATION: Synthetic sequence

<400> SEQUENCE: 9
gataagggat tgggat                                                   16

<210> SEQ ID NO 10
<211> LENGTH: 16
<212> TYPE: DNA
<213> ORGANISM: Artificial Sequence
<220> FEATURE:
<223> OTHER INFORMATION: Synthetic sequence

<400> SEQUENCE: 10
ggtaggtgta ggattt                                                   16

<210> SEQ ID NO 11
<211> LENGTH: 16
<212> TYPE: DNA
<213> ORGANISM: Artificial Sequence
<220> FEATURE:
<223> OTHER INFORMATION: Synthetic sequence

<400> SEQUENCE: 11
ggttaggtgt aggttt                                                   16

<210> SEQ ID NO 12
<211> LENGTH: 16
<212> TYPE: DNA
<213> ORGANISM: Artificial Sequence
<220> FEATURE:
<223> OTHER INFORMATION: Synthetic sequence

<400> SEQUENCE: 12
ggttaggtgg aggttt                                                   16

<210> SEQ ID NO 13
<211> LENGTH: 16
<212> TYPE: DNA
```

<213> ORGANISM: Artificial Sequence
<220> FEATURE:
<223> OTHER INFORMATION: Synthetic sequence

<400> SEQUENCE: 13
ggttaggttt aggttt                                                        16

<210> SEQ ID NO 14
<211> LENGTH: 16
<212> TYPE: DNA
<213> ORGANISM: Artificial Sequence
<220> FEATURE:
<223> OTHER INFORMATION: Synthetic sequence

<400> SEQUENCE: 14
ggttaggtta aggtta                                                        16

<210> SEQ ID NO 15
<211> LENGTH: 16
<212> TYPE: DNA
<213> ORGANISM: Artificial Sequence
<220> FEATURE:
<223> OTHER INFORMATION: Synthetic sequence

<400> SEQUENCE: 15
ggttggttgg ttggtt                                                        16

<210> SEQ ID NO 16
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Portion of human telomeric sequence

<400> SEQUENCE: 16
ttagggttag                                                               10

<210> SEQ ID NO 17
<211> LENGTH: 10
<212> TYPE: DNA
<213> ORGANISM: Artificial Sequence
<220> FEATURE:
<223> OTHER INFORMATION: Synthetic sequence

<400> SEQUENCE: 17
tagggttagg                                                               10

<210> SEQ ID NO 18
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Portion of human telomeric sequence

<400> SEQUENCE: 18
agggttaggg                                                               10

<210> SEQ ID NO 19
<211> LENGTH: 10
<212> TYPE: DNA
<213> ORGANISM: Homo sapiens
<220> FEATURE:
<221> NAME/KEY: misc_feature -continued
<222> LOCATION: (1)..(10)
<223> OTHER INFORMATION: Portion of human telomeric sequence

<400> SEQUENCE: 19
gggttagggt                                                                  10

<210> SEQ ID NO 20
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Portion of human telomeric sequence

<400> SEQUENCE: 20
ggttagggtt                                                                  10

<210> SEQ ID NO 21
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Portion of human telomeric sequence

<400> SEQUENCE: 21
gttagggtta                                                                  10

<210> SEQ ID NO 22
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 22
ttagggttag g                                                                11

<210> SEQ ID NO 23
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 23
tagggttagg g                                                                11

<210> SEQ ID NO 24
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 24
agggttaggg t                                                                11

<210> SEQ ID NO 25

```
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 25
gggttagggt t                                                              11

<210> SEQ ID NO 26
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Portion of human telomeric sequence

<400> SEQUENCE: 26
ggttagggtt a                                                              11

<210> SEQ ID NO 27
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 27
ttagggttag gg                                                             12

<210> SEQ ID NO 28
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 28
tagggttagg gt                                                             12

<210> SEQ ID NO 29
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 29
agggttaggg tt                                                             12

<210> SEQ ID NO 30
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 30
```
gggttagggt ta                                                    12

<210> SEQ ID NO 31
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 31
ggttagggtt ag                                                    12

<210> SEQ ID NO 32
<211> LENGTH: 12
<212> TYPE: DNA
<213> ORGANISM: Homo sapiens
<220> FEATURE:
<221> NAME/KEY: misc_feature
<222> LOCATION: (1)..(12)
<223> OTHER INFORMATION: Portion of human telomeric sequence

<400> SEQUENCE: 32
gttagggtta gg                                                    12

<210> SEQ ID NO 33
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Portion of human telomeric sequence

<400> SEQUENCE: 33
ttagggttag ggt                                                   13

<210> SEQ ID NO 34
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Portion of human telomeric sequence

<400> SEQUENCE: 34
tagggttagg gtt                                                   13

<210> SEQ ID NO 35
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Portion of human telomeric sequence

<400> SEQUENCE: 35
agggttaggg tta                                                   13

<210> SEQ ID NO 36
<211> LENGTH: 13
<212> TYPE: DNA
<213> ORGANISM: Homo sapiens
<220> FEATURE:

```
<221> NAME/KEY: misc_feature
<222> LOCATION: (1)..(13)
<223> OTHER INFORMATION: Portion of human telomeric sequence

<400> SEQUENCE: 36
gggttagggt tag                                                           13

<210> SEQ ID NO 37
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Portion of human telomeric sequence

<400> SEQUENCE: 37
ggttagggtt agg                                                           13

<210> SEQ ID NO 38
<211> LENGTH: 13
<212> TYPE: DNA
<213> ORGANISM: Homo sapiens
<220> FEATURE:
<221> NAME/KEY: misc_feature
<222> LOCATION: (1)..(13)
<223> OTHER INFORMATION: Portion of human telomeric sequence

<400> SEQUENCE: 38
gttagggtta ggg                                                           13

<210> SEQ ID NO 39
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 39
ttagggttag ggtt                                                          14

<210> SEQ ID NO 40
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 40
tagggttagg gtta                                                          14

<210> SEQ ID NO 41
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 41
agggttaggg ttag                                                          14
```

```
<210> SEQ ID NO 42
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 42
gggttagggt tagg                                              14

<210> SEQ ID NO 43
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 43
ggttagggtt aggg                                              14

<210> SEQ ID NO 44
<211> LENGTH: 14
<212> TYPE: DNA
<213> ORGANISM: Homo sapiens
<220> FEATURE:
<221> NAME/KEY: misc_feature
<222> LOCATION: (1)..(14)
<223> OTHER INFORMATION: Portion of human telomeric sequence

<400> SEQUENCE: 44
gttagggtta gggt                                              14

<210> SEQ ID NO 45
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence

<400> SEQUENCE: 45
ttagggttag ggtta                                             15

<210> SEQ ID NO 46
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence

<400> SEQUENCE: 46
tagggttagg gttag                                             15

<210> SEQ ID NO 47
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence
```

```
<400> SEQUENCE: 47
agggttaggg ttagg                                                    15

<210> SEQ ID NO 48
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence

<400> SEQUENCE: 48
gggttagggt taggg                                                    15

<210> SEQ ID NO 49
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: Portion of human telomeric sequence

<400> SEQUENCE: 49
ggttagggtt agggt                                                    15

<210> SEQ ID NO 50
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Portion of human telomeric sequence

<400> SEQUENCE: 50
ttagggttag ggttag                                                   16

<210> SEQ ID NO 51
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Portion of human telomeric sequence

<400> SEQUENCE: 51
tagggttagg gttagg                                                   16

<210> SEQ ID NO 52
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Portion of human telomeric sequence

<400> SEQUENCE: 52
agggttaggg ttaggg                                                   16

<210> SEQ ID NO 53
<211> LENGTH: 16
<212> TYPE: DNA
<213> ORGANISM: Homo sapiens
```

```
<220> FEATURE:
<221> NAME/KEY: misc_feature
<222> LOCATION: (1)..(16)
<223> OTHER INFORMATION: Portion of human telomeric sequence

<400> SEQUENCE: 53
gggttagggt tagggt                                                         16

<210> SEQ ID NO 54
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: Portion of human telomeric sequence

<400> SEQUENCE: 54
ggttagggtt agggtt                                                         16

<210> SEQ ID NO 55
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 55
ttagggttag ggttagg                                                        17

<210> SEQ ID NO 56
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 56
tagggttagg gttaggg                                                        17

<210> SEQ ID NO 57
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 57
agggttaggg ttaggt                                                         17

<210> SEQ ID NO 58
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 58
gggttagggt tagggtt                                                        17
```

```
<210> SEQ ID NO 59
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 59
ggttagggtt agggtta                                                  17

<210> SEQ ID NO 60
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Portion of human telomeric sequence

<400> SEQUENCE: 60
gttagggtta gggttag                                                  17

<210> SEQ ID NO 61
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence

<400> SEQUENCE: 61
ttagggttag ggttaggg                                                 18

<210> SEQ ID NO 62
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence

<400> SEQUENCE: 62
tagggttagg gttagggt                                                 18

<210> SEQ ID NO 63
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence

<400> SEQUENCE: 63
agggttaggg ttagggtt                                                 18

<210> SEQ ID NO 64
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence
```

<400> SEQUENCE: 64
gggttagggt tagggtta                                          18

<210> SEQ ID NO 65
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence

<400> SEQUENCE: 65
ggtTagggtt agggttag                                          18

<210> SEQ ID NO 66
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Portion of human telomeric sequence

<400> SEQUENCE: 66
gttagggtta gggttagg                                          18

<210> SEQ ID NO 67
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 67
ttagggttag ggttagggt                                         19

<210> SEQ ID NO 68
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 68
tagggttagg gttagggtt                                         19

<210> SEQ ID NO 69
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 69
agggttaggg ttagggtta                                         19

<210> SEQ ID NO 70
<211> LENGTH: 19
<212> TYPE: DNA

```
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 70
gggttagggt tagggttag                                               19

<210> SEQ ID NO 71
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 71
ggttagggtt agggttagg                                               19

<210> SEQ ID NO 72
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Portion of human telomeric sequence

<400> SEQUENCE: 72
gttagggtta gggttaggg                                               19

<210> SEQ ID NO 73
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 73
ttagggttag ggttagggtt                                              20

<210> SEQ ID NO 74
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 74
tagggttagg gttagggtta                                              20

<210> SEQ ID NO 75
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 75
agggttaggg ttagggttag                                              20
```

```
<210> SEQ ID NO 76
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 76
gggttagggt tagggttagg                                               20

<210> SEQ ID NO 77
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 77
ggttagggtt agggttaggg                                               20

<210> SEQ ID NO 78
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Portion of human telomeric sequence

<400> SEQUENCE: 78
gttagggtta gggttagggt                                               20

<210> SEQ ID NO 79
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Portion of human telomeric sequence

<400> SEQUENCE: 79
ttagggttag ggtttagggtt a                                            21

<210> SEQ ID NO 80
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Portion of human telomeric sequence

<400> SEQUENCE: 80
tagggttagg gttagggtta g                                             21

<210> SEQ ID NO 81
<211> LENGTH: 21
<212> TYPE: DNA
<213> ORGANISM: Homo sapiens
<220> FEATURE:
<221> NAME/KEY: misc_feature
<222> LOCATION: (1)..(21)
```

```
<223> OTHER INFORMATION: Portion of human telomeric sequence

<400> SEQUENCE: 81
agggttaggg ttagggttag g                                         21

<210> SEQ ID NO 82
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Portion of human telomeric sequence

<400> SEQUENCE: 82
gggttagggt tagggttagg g                                         21

<210> SEQ ID NO 83
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Portion of human telomeric sequence

<400> SEQUENCE: 83
ggttagggtt agggttaggg t                                         21

<210> SEQ ID NO 84
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Portion of human telomeric sequence

<400> SEQUENCE: 84
gttagggtta gggttagggt t                                         21

<210> SEQ ID NO 85
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 85
ttagggttag ggttagggtt ag                                        22

<210> SEQ ID NO 86
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 86
tagggttagg gttagggtta gg                                        22

<210> SEQ ID NO 87
<211> LENGTH: 22
```

-continued

```
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 87
agggttaggg ttagggttag gg                                          22

<210> SEQ ID NO 88
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 88
gggttagggt tagggttagg gt                                          22

<210> SEQ ID NO 89
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 89
ggttagggtt agggttaggg tt                                          22

<210> SEQ ID NO 90
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Portion of human telomeric sequence

<400> SEQUENCE: 90
gttagggtta gggttagggt ta                                          22

<210> SEQ ID NO 91
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 91
ttagggttag ggttagggtt agg                                         23

<210> SEQ ID NO 92
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 92
```
tagggttagg gttagggtta ggg                                            23

<210> SEQ ID NO 93
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 93
agggttaggg ttagggttag ggt                                            23

<210> SEQ ID NO 94
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 94
gggttagggt tagggttagg gtt                                            23

<210> SEQ ID NO 95
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 95 ggtagggtt agggttaggg tta                                             23

<210> SEQ ID NO 96
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Portion of human telomeric sequence

<400> SEQUENCE: 96
gttagggtta gggttagggt tag                                            23

<210> SEQ ID NO 97
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Portion of human telomeric sequence

<400> SEQUENCE: 97
ttagggttag ggttagggtt aggg                                           24

<210> SEQ ID NO 98
<211> LENGTH: 24
<212> TYPE: DNA
<213> ORGANISM: Homo sapiens
<220> FEATURE:
<221> NAME/KEY: misc_feature

```
<222> LOCATION: (1)..(24)
<223> OTHER INFORMATION: Portion of human telomeric sequence

<400> SEQUENCE: 98
tagggttagg gttagggtta gggt                                              24

<210> SEQ ID NO 99
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Portion of human telomeric sequence

<400> SEQUENCE: 99
agggttaggg ttagggttag ggtt                                              24

<210> SEQ ID NO 100
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Portion of human telomeric sequence

<400> SEQUENCE: 100
gggttagggt tagggttagg gtta                                              24

<210> SEQ ID NO 101
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Portion of human telomeric sequence

<400> SEQUENCE: 101
ggttagggtt agggttaggg ttag                                              24

<210> SEQ ID NO 102
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Portion of human telomeric sequence

<400> SEQUENCE: 102
gttagggtta gggttagggt tagg                                              24

<210> SEQ ID NO 103
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 103
ttagggttag ggttagggtt agggt                                             25

<210> SEQ ID NO 104
```

```
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 104
tagggttagg gttagggtta gggtt                                            25

<210> SEQ ID NO 105
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 105
agggttaggg ttagggttag ggtta                                            25

<210> SEQ ID NO 106
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 106
gggttagggt tagggttagg gttag                                            25

<210> SEQ ID NO 107
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 107
ggttagggtt agggttaggg ttagg                                            25

<210> SEQ ID NO 108
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: Portion of human telomeric sequence

<400> SEQUENCE: 108
gttagggtta gggttagggt taggg                                            25

<210> SEQ ID NO 109
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 109
```
ttagggttag ggttagggtt agggtt                                         26

<210> SEQ ID NO 110
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 110
tagggttagg gttagggtta gggtta                                         26

<210> SEQ ID NO 111
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 111
agggttaggg ttagggttag ggttag                                         26

<210> SEQ ID NO 112
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 112
gggttagggt tagggttagg gttagg                                         26

<210> SEQ ID NO 113
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 113
ggttagggtt agggttaggg ttaggg                                         26

<210> SEQ ID NO 114
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Portion of human telomeric sequence

<400> SEQUENCE: 114
gttagggtta gggttagggt tagggt                                         26

<210> SEQ ID NO 115
<211> LENGTH: 27
<212> TYPE: DNA
<213> ORGANISM: Homo sapiens
<220> FEATURE:

```
<221> NAME/KEY: misc_feature
<222> LOCATION: (1)..(27)
<223> OTHER INFORMATION: Portion of human telomeric sequence

<400> SEQUENCE: 115
ttagggttag ggttagggtt agggtta                                        27

<210> SEQ ID NO 116
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Portion of human telomeric sequence

<400> SEQUENCE: 116
tagggttagg gttagggtta gggttag                                        27

<210> SEQ ID NO 117
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Portion of human telomeric sequence

<400> SEQUENCE: 117
agggttaggg ttagggttag ggttagg                                        27

<210> SEQ ID NO 118
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Portion of human telomeric sequence

<400> SEQUENCE: 118
gggttagggt tagggttagg gttaggg                                        27

<210> SEQ ID NO 119
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Portion of human telomeric sequence

<400> SEQUENCE: 119
ggttagggtt agggttaggg ttagggt                                        27

<210> SEQ ID NO 120
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: Portion of human telomeric sequence

<400> SEQUENCE: 120
gttagggtta gggttagggt tagggtt                                        27
```

<210> SEQ ID NO 121
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 121
ttagggttag ggttagggtt agggttag                                    28

<210> SEQ ID NO 122
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 122
tagggttagg gttagggtta gggttagg                                    28

<210> SEQ ID NO 123
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 123
agggttaggg ttagggttag ggttaggg                                    28

<210> SEQ ID NO 124
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 124
gggttagggt tagggttagg gttagggt                                    28

<210> SEQ ID NO 125
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 125
ggttagggtt agggttaggg ttagggtt                                    28

<210> SEQ ID NO 126
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Portion of human telomeric sequence

<400> SEQUENCE: 126
gttagggtta gggttagggt tagggtta        28

<210> SEQ ID NO 127
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Portion of human telomeric sequence

<400> SEQUENCE: 127
ttagggttag ggttagggtt agggttagg        29

<210> SEQ ID NO 128
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Portion of human telomeric sequence

<400> SEQUENCE: 128
tagggttagg gttagggtta gggttaggg        29

<210> SEQ ID NO 129
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Portion of human telomeric sequence

<400> SEQUENCE: 129
agggttaggg ttagggttag ggttagggt        29

<210> SEQ ID NO 130
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Portion of human telomeric sequence

<400> SEQUENCE: 130
gggttagggt tagggttagg gttagggtt        29

<210> SEQ ID NO 131
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Portion of human telomeric sequence

<400> SEQUENCE: 131
ggttagggtt agggttaggg ttagggtta        29

<210> SEQ ID NO 132
<211> LENGTH: 29
<212> TYPE: DNA
<213> ORGANISM: Homo sapiens

```
<220> FEATURE:
<221> NAME/KEY: misc_feature
<222> LOCATION: (1)..(29)
<223> OTHER INFORMATION: Portion of human telomeric sequence

<400> SEQUENCE: 132
gttagggtta gggttagggt tagggttag                                         29

<210> SEQ ID NO 133
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 133
ttagggttag ggttagggtt agggttaggg                                        30

<210> SEQ ID NO 134
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 134
tagggttagg gttagggtta gggttagggt                                        30

<210> SEQ ID NO 135
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 135
agggttaggg ttagggttag ggttagggtt                                        30

<210> SEQ ID NO 136
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 136
gggttagggt tagggttagg gttagggtta                                        30

<210> SEQ ID NO 137
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 137
ggttagggtt agggttaggg ttagggttag                                        30
```

```
<210> SEQ ID NO 138
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: Portion of human telomeric sequence

<400> SEQUENCE: 138
gttagggtta gggttagggt tagggttagg                                       30
```